United States Patent
Ow et al.

(10) Patent No.: US 11,549,922 B2
(45) Date of Patent: Jan. 10, 2023

(54) TRACER ANALYSIS

(71) Applicant: Saudi Arabian Oil Company, Dhahran (SA)

(72) Inventors: Hooisweng Ow, Woburn, MA (US); Gawain Thomas, Somerville, MA (US); Sehoon Chang, Boston, MA (US); Wei Wang, Quincy, MA (US)

(73) Assignee: Saudi Arabian Oil Company, Dhahran (SA)

( * ) Notice: Subject to any disclaimer, the term of this patent is extended or adjusted under 35 U.S.C. 154(b) by 196 days.

(21) Appl. No.: 16/938,801

(22) Filed: Jul. 24, 2020

(65) Prior Publication Data

US 2021/0025858 A1    Jan. 28, 2021

Related U.S. Application Data

(60) Provisional application No. 62/878,281, filed on Jul. 24, 2019.

(51) Int. Cl.
    *G01N 30/74* (2006.01)
    *G01N 21/64* (2006.01)
    (Continued)

(52) U.S. Cl.
    CPC ......... *G01N 30/74* (2013.01); *G01N 21/6428* (2013.01); *G01N 33/1833* (2013.01);
    (Continued)

(58) Field of Classification Search
    None
    See application file for complete search history.

(56) References Cited

U.S. PATENT DOCUMENTS

| 4,772,563 A | 9/1988 | Evangelista et al. |
| 6,691,780 B2 | 2/2004 | Nguyen et al. |

(Continued)

FOREIGN PATENT DOCUMENTS

| EP | 2480625 A4 | 4/2013 |
| EP | 2480626 A4 | 4/2013 |

(Continued)

OTHER PUBLICATIONS

Cai, X. et al. Two-dimensional liquid chromatography separation of peptides using reversed-phase/weak cation-exchange mixed-mode column in first dimension, Journal of Chromatography A, vol. 1228, pp. 242-249 (Year: 2012).*

(Continued)

*Primary Examiner* — Xiaoyun R Xu
(74) *Attorney, Agent, or Firm* — Fish & Richardson P.C.

(57) ABSTRACT

Systems and methods for analyzing groundwater samples with multiple organic tracer species from a petroleum containing reservoir include obtaining the sample, isolating an aqueous fraction of the groundwater sample, separating the aqueous fraction into a plurality of components, where each component corresponds to a different one of the organic tracer species, combining each of the separated components with at least one lanthanide element to form a plurality of component solutions, where a ratio of the at least one lanthanide element to the separated component in each component solution is 5:1 or greater, and analyzing each component solution to determine a relative amount of each organic tracer species in the groundwater sample.

30 Claims, 19 Drawing Sheets

(51) Int. Cl.
G01N 33/18 (2006.01)
G01N 30/02 (2006.01)
(52) U.S. Cl.
CPC .............. G01N 2021/6439 (2013.01); G01N 2030/027 (2013.01)

(56) References Cited

U.S. PATENT DOCUMENTS

| | | | |
|---|---|---|---|
| 8,627,902 | B2 | 1/2014 | Hammer |
| 9,366,099 | B2 | 6/2016 | Ly |
| 2004/0108110 | A1 | 6/2004 | Zupanick et al. |
| 2005/0252286 | A1 | 11/2005 | Ibrahim et al. |
| 2009/0087911 | A1 | 4/2009 | Rogerio |
| 2009/0087912 | A1 | 4/2009 | Ramos et al. |
| 2009/0248309 | A1 | 10/2009 | Nelville et al. |
| 2010/0049625 | A1 | 2/2010 | Biebesheimer et al. |
| 2012/0062886 | A1 | 3/2012 | Piotti et al. |
| 2012/0115128 | A1 | 5/2012 | Miller |
| 2012/0193578 | A1 | 8/2012 | Pan et al. |
| 2012/0261617 | A1 | 10/2012 | Pan et al. |
| 2012/0325465 | A1 | 12/2012 | Hammer et al. |
| 2013/0084643 | A1 | 4/2013 | Commarieu et al. |
| 2014/0231077 | A1 | 8/2014 | Rivero et al. |
| 2014/0260694 | A1 | 9/2014 | Szlendak |
| 2015/0132543 | A1 | 5/2015 | Nouzille et al. |
| 2016/0003040 | A1 | 1/2016 | Jessheim et al. |
| 2017/0059668 | A1 | 3/2017 | Chang et al. |
| 2017/0199124 | A1 | 7/2017 | Bolduc et al. |
| 2018/0171782 | A1* | 6/2018 | Cox .................... E21B 47/11 |
| 2019/0218907 | A1 | 7/2019 | Ow et al. |
| 2019/0226326 | A1 | 7/2019 | Ow et al. |
| 2019/0368336 | A1 | 12/2019 | Hammond et al. |

FOREIGN PATENT DOCUMENTS

| | | |
|---|---|---|
| GB | 2489714 A | 10/2012 |
| WO | 2010138914 A2 | 12/2010 |
| WO | 2011035292 A2 | 3/2011 |
| WO | 2011035294 A2 | 3/2011 |
| WO | 2011035294 A3 | 7/2011 |
| WO | 2011035292 A3 | 10/2011 |
| WO | 2014207075 A2 | 12/2014 |
| WO | 2015097116 A1 | 7/2015 |
| WO | 2015200060 A2 | 12/2015 |
| WO | 2017136641 A1 | 8/2017 |
| WO | 2018085504 A1 | 5/2018 |
| WO | 2018175763 A1 | 9/2018 |

OTHER PUBLICATIONS

GCC Examination Report issued in Gulf Cooperation Council Appln. No. 2020-40154, dated Nov. 7, 2021, 4 pages.
Thomas et al., "Deployment and Detection of a Novel Barcoded Advanced Tracers System for the Optimization of Improved Waterflood Recovery in Hydrocarbon Reservoirs" SPE-194872-MS, SPE Middle East Oil and Gas Show and Conference. Society of Petroleum Engineers, 2019, 10 pages.
PCT International Search Report and Written Opinion in International Application. No. PCT/US2020/043,386, dated Nov. 6, 2020, 16 pages.
Agenet et al., "SPE 157019: Fluorescent Nanobeads: a First Step Toward Intelligent Water Tracers," Society of Petroleum Engineers, SPE International Oilfield Nanotechnology conference, Jun. 12-14, 2012, 13 pages.
Anisimov, "SPE 118862: The Use of Tracers for Reservoir Characterization," Society of petroleum Engineers (SPE), presented at SPE Middle East Oil and Gas Show and Conference, Mar. 15-18, 2009, 8 pages.
Armelao et al., "Design of luminescent lanthanide complexes: From molecules to highly efficient photo-emitting materials," Coordination Chemistry Reviews, vol. 254, 5-6, Mar. 2010, 19 pages.

Aslan et al., "Fluorescent Core-Shell AG@SiO2 Nanocomposites for Metal-Enhanced Fluorescence and Single Nanoparticle Sensing Platforms," Jan. 19, 2007, 2 pages.
Bünzli and Piguet, "Taking advantage of luminescent lanthanide ions," Chemical Society Reviews, vol. 34, Issue 12, Sep. 2005, 30 pages.
Chang et al., "Magnetic SERS Composite Nanoparticles for Microfluidic Detection," 251st ACE National Meeting, Mar. 13-17, 2016, 1 pages.
Chen et al., "FITC functionalized magnetic core-shell Fe3O4/ Ag hybrid nanoparticle for selective determination of molecular biothiols," Elsevier Ltd., Dec. 2013, 7 pages.
Chen et al., "Impact of Irreversible Retention on Tracer Deployments; Constraining Novel Material Deployments," SPE 188890-MS, in SPE Abu Dhabi International Petroleum Exhibition and Conference, Society of Petroleum Engineers, Nov. 2017, 8 pages.
Chen et al., "Improved Reservoir History Matching and Prudction Optimization with Tracer Data," SPE 191523-MS, in SPE Annual Technical Conference and Exhibition, Society of Petroleum Engineers, Sep. 2018, 15 pages.
Chuang et al., "Ultra-sensitive in-situ detection of novel near-infrared persistent luminescent tracer nanoagents in crude oil-water mixtures," a natureresearchjournal, Scientific Reports, Jun. 15, 2016, 5 pages.
Cubillos et al., "SPE 174394-MS: The Value of Inter-well and Single Well Tracer Technology for De-Risking and Optimizing a CEOR Process—Caracara Field Case," Society of Petroleum Engineers (SPE), presented at EUROPEC 2015, Jun. 1-4, 2015, 19 pages.
Das et al., "Molecular Fluorescence, Phosphorescence, and Chemiluminescence Spectrometry," Analytical Chemistry, Nov. 3, 2011, 29 pages.
Deans, "SPE 7076: Using Chemical Tracers to Measure Fractional Flow and Saturation In-Situ,"Society of Petroleum Engineers (SPE), presented at SPE Symposium on improved Methods of Oil Recovery, Apr. 16-17, 1978, 10 pages.
Deschamps et al., "Drilling to the Extreme: the Micro-Coring Bit Concept," IADC/SPE 115187, presented at the IADC/SPE Asai Pacific Drilling Technology Conference and Exhibition, Aug. 25-27, 2008, 12 pages.
Desmette et al., "Drilling Hard and Abrasive Rock Efficiently, or Generating Quality Cuttings? You no Longer Have to Choose . . . ," SPE 116554, Societv of Petroleum Engineers, 2008 SPE Annual Technical Conference and Exhibition, Sep. 21-24, 2008, 19 pages.
Du and Guan, "Interwell tracer tests: lessons learnted from past field studies," SPE 93140-MS, in SPE Asia Pacific Oil and Gas Conference and Exhibition, Society of Petroleum Engineers, Apr. 5-7, 2005, 9 pages.
Dugstad, "Chapter 6: Well-to-well tracer tests," in Petroleum Engineering Handbook, 5, pp. 651-683, 2007, 31 pages.
El-Aneed et al., "Mass Spectrometry, Review of the Basics: Electrospray, MALDI, and Commonly Used Mass Analyzers," Anplied Spectroscopy Reviews, Mar. 16, 2009, 22 pages.
Fichtel et al., "A highly sensitive HPLC method for determination of nanomolar concentrations of dipicolinic acid, a characteristic constituent of bacterial endospores" Journal of Microbiological Methods (2007), 70, 319-327, 9 pages.
Freeze and Cherry, "Chapter 9: Groundwater Contamination," in Groundwater, Englewood Cliffs, NJ: Prentice-Hall, Inc., p. 604, 1979, 80 pages.
Galdiga and Greibrokk, "Ultra-trace determination of flurinated aromatic carboxylic acids in aqueous reservoir fluids using solid-phase extraction in combination with gas chromatography-mass spectrometry," Journal of Chromatography, vol. 793, Issue 2, Jan. 16, 1998, 10 pages.
Gardiner et al., "Practical Raman Spectroscopy," Springer-Verlag, 1989, 9 pages.
George et al., "Modified Dipicolinic Acid Ligands for Sensitation and Europium (III) Luminescence," Inorganic Chemistry, vol. 45, No. 4, Feb. 1, 2006, 6 pages.
Georgi, et al., "Advances in Cuttings Collection and Analysis," SPWLA 34th Annual Logging Symposium, Jun. 13-16, 1993, 20 pages.

(56) References Cited

OTHER PUBLICATIONS

Hagoot, "The response of interwell tracer tests in watered-out reservoirs," SPE 11131-MS, in SPE Annual Technical Conference and Exhibition, Society of Petroleum Engineers, Jan. 1982, 21 pages.

Han et al., "Application of Silver-Coated Magnetic Microspheres to a SERS-Based Optofluidic Sensor," The Journal of Physical Chemistry (JPCC), Mar. 7, 2011, 7 pages.

Hindle et al., "Dipicolinic acid (DPA) assay revisited and appraised for spore detection," Analyst, 1999, 124: 1599-1604, 6 pages.

Hu et al., "Smart Liquid SERS Substrates based on $Fe_3O_4$/ Au Nanoparticles with Reversibility Tunable Enhancement Factor for Practical Quantitative Detection," a naturere search journal, Scientific Reports, Nov. 27, 2014, 10 pages.

Huseby et al., "Assessing EOR potential from partitioning tracer data," SPE 172808-MS, in SPE Middle East Oil and Gas Show and Conference, Society of Petroleum Engineers, Mar. 2015, 15 pages.

Huseby et al., "SPE-169183-MS: High Quality Flow Information from Tracer Data," Society of Petroleum Engineers (SPE), presented at the SPE Bergen One Day Seminar, Apr. 2, 2014, 9 pages.

Hutchins et al., "SPE-21049: Aqueous Tracers for Oilfield Applications," Society of Petroleum Engineers (SPE), presented at SPE International Symposium on Oilfield Chemistry, Feb. 20-22, 1991, 9 pages.

International Search Report and Written Opinion in International Application No. PCT/US2017/064,414 dated Feb. 27, 2018, 17 pages.

Invitation to Pay Additional Fees and, Where Applicable, Protest Fee issued in International Application No. PCT/US2019/014166 dated Jun. 3, 2019, 16 pages.

Jenkins et al., "Ultratrace Determination of Selected Lanthanides by Luminescence Enhancement," Analytical Chemistry, vol. 68, No. 17, Jan. 1, 1996, 7 pages.

Jun et al., "Multifunctional Silver-Embedded Magnetic Nanoparticles as SERS Nanoprobes and Their Annlications," Wiley-VCR Verlag GmbH& Co. KGaA, Weinheim, Jan. 4, 2010, 7 pages.

Khan et al., "Optimizing waterflood management in a giant UAE carbonate oil field using simulation-based streamlines," SPE 171777-MS, in Abu Dhabi International Petroleum Exhibition and Conference, Society of Petroleum Engineers, Nov. 10-13, 2014, 9 pages.

Kneipp et al., "Single Molecule Detection Using Surface-Enhanced Raman Scattering (SERS)," Physical Review Letters, American Physical Society vol. 78, No. 9, Mar. 3, 1997, 4 pages.

Kornberger and Thiele, "Experiences with an Efficient Rate-Management Approach for the 8th Tortonian Reservoir in the Vienna Basin," SPE 166393-PA, SPE Reservoir Evaluation and Engineering, vol. 17, No. 2, May 2014, 12 pages.

Kosynkin and Alaskar, "Oil Industry First Interwell Trial of Reservoir Nanoagent Tracers," SPE 181551-MS, in SPE Annual Technical Conference and Exhibition, Society of Petroleum Engineers, Sep. 2016, 15 pages.

Lomstein and Jorgensen, "Pre-column liquid chromatographic determination of dipicolinic acid from bacterial endospores," Limnology and Oceanography: Methods, Apr. 2012, 10:4, 227-233, 14 pages.

Marchetti et al., "Fluorous affinity chromatography for enrichment and determination of perfluoroalkyl substances," Annual Review of Analytical Chemistry vol. 84, Jul. 19, 2012, 8 pages.

Moyner et al., "The Application of Flow Diagnostics for Reservoir Management," Society of Petroleum Engineers (SPE), Apr. 2015, 18 pages.

Muller and Seubert, "Ultra trace determination of fluorobenzoic acids in tap and reservoir water using solid-phase extraction and gas chromatography-mass spectrometry," Journal of Chromatography A, 1260, Oct. 2012, 7 pages.

Parker and Williams, "Getting excited about lanthanide complexation chemistry," Journal of the Chemical Society, Dalton Transactions, vol. 18, 1996, 16 pages.

Parker et al., "Being excited by lanthanide coordination complexes: aqua species, chirality, excited-state chemistry, and exchange dynamics," Chemical Reviews, vol. 102, Issue 6, May 2002, 34 pages.

PCT International Search Report and Written Opinion in International Appln. No. PCT/US2019/056059, dated Feb. 21, 2020, 15 pages.

Petoud et al., "Brilliant SM, Eu, Tb, and Dy Chiral Lanthanide Complexes with Strong Circularly Polarized Luminescence," Journal fo the American Chemical Society (JACS), Dec. 15, 2006, 7 pages.

Rowan et al., "Dynamic Covalent Chemistry," Angewante Chemie International Edition, Mar. 15, 2002, 55 pages.

Sabbatini et al., "Luminescent lanthanide complexes as photochemical supramolecular devices." Coordination Chemistry Reviews, vol. 123, issue 1-2, Feb. 1993, 28 pages.

Sammes and Yshioglu, "Modern bioassays using metal chelates as luminescent probes." Natural Product Reports, vol. 31, No. 1, 1996, 28 pages.

Sanni et al., "A field case study of inter-well chemical tracer test," in SPE International Symposium on Oilfield Chemistry, Society of Petroleum Engineers, Apr. 2015, 17 pages.

Sanni et al., "Pushing the envelope of residual oil measurement: A field case study of a new class of inter-well chemical tracers," Journal of Petroleum Science and Engineering, vol. 163, 2018, 19 pages.

Santarelli et al., "Formation Evaluation From Logging on Cuttings," SPE Reservoir Evaluation and Engineering, presented at the 1996 SPE Permian Basin Oil and Gas Recovery Conference, Mar. 27-29, 1996, published Jun. 1998, 7 pages.

Selvin et al., "Principles and biophysical applications of lanthanide-based probes," Annual Review of Biophysics and Biomolecular Structure, Jun. 2002, 28 pages.

Serres-Piole et al., "Direct sensitive simultaneous determination of fluorinated benzoic acids in oil reservoir waters by ultra high-performance liquid chromatography—tandem mass spectrometry," Journal of Chromatography A, 1218, Aug. 2011, 5872-5877, 6 pages.

Serres-Piole et al., "Water Tracers in Oilfield Applications: Guidelines" Journal of Petroleum Science and Engineering, 2012, 22-39, 18 pages.

Shook et al., "SPE 124614: Determining Reservoir Properties and Flood Performance from Tracer Test Analysis," Society of petroleum Engineers (SPE), presented at SPE Annual Technical Conference and Exhibition, Oct. 4-7, 2009, 19 pages.

Song et al., "SERS-Fncoded Nano gapped Plasmonic Nanoparticles: Growth of Metallic Nanoshell by Templating Redox-Active Polymer Brushes," Journal of the American Chemical Society (JACS), Apr. 28, 2014, 4 pages.

Stiles et al., "Surface-enhanced Raman Spectroscopy," Annual Review of Analytical Chemistry, Mar. 18, 2008, 29 pages.

Stryer et al., "Diffusion-enhanced fluorescence energy transfer," Annual Review of Biophysics and bioengineering, vol. 11, Issue 1, 1982, 21 pages.

Tang et al., "Synthesis ofNovel Derivatives of Pyridine-2,6-dicarboxylic Acid," Synthetic Communications: An International Journal for Rapid Communication of Synthetic Organic Chemistry, 36(14), 2027-2034, Jun. 2006, 9 pages.

Tian et al., "Off-Resonant Gold Superstructures as Ultrabright Minimally Invasive Surface-Enhanced Raman Scattering (SERS) Probes," American Chemical Society, Jul. 2015, 7 pages.

Toulhoat, "Experimentation and Modelling of U, Th and Lanthanides Transport in Fissured Rocks: Influence of Complexation," MRS Proceedings, vol. 50, Jan. 1, 1985, 8 pages.

Wang et al., "The Design and Implementation of a Full Field Inter-Well Tracer Program on a Giant UAE Carbonate Oil Field," in Abu Dhabi International Petroleum Exhibition and Conference, Society of Petroleum Engineers, SPE-177527-MS, Nov. 2015, 8 pages.

Wu et al., "A reusable biosensor chip for SERS-fluorescence dual mode immunoassay," Proc. SPIE 9543, Third International Symposium on Laser Interaction with Matter, 954317, May 4, 2015, 6 pages.

Wu et al., "A SERS-Assisted 3D Barcode Chip for High-Throughput Bio sensing," Small Journal vol. 11, No. 23, Jun. 11, 2015, 9 pages.

(56) References Cited

OTHER PUBLICATIONS

Xu et al.., "Measurement of two-photon excitation cross sections of molecular fluorophores with data from 690 to 1050 nm," Journal of the Optical Society of America B, Mar. 1996, 11 pages.

Yang et al., "The Co-Luminescence Groups of Sm-La-pyridyl Carboxylic Acids and the Binding Characteristics between the Selected Doped Complex and Bovine Serum Albumin," Bulletin of the Korean Chemical Society 33(4), 1303-1309, Apr. 20, 2012, 7 pages.

Zaberi et al., "SPE 166005: Improved Reservoir Surveillance Through Injected Tracers in a Saudi Arabian Field: Case Study," Society of Petroleum Engineers (SPE), presented at SPE Reservoir Characterization and Simulation Conference and Exhibition, Sep. 16-18, 2013, 15 pages.

Zemel, "Chapter 3: Interwell Water Tracers," Tracers in the Oil Field, vol. 43, 1st Edition, Elsevier Science, Jan. 1995, 47 pages.

Zhou et al., "Upconversion luminescent materials: advances and applications," Chem Rev., Jan. 14, 2015, 71 pages.

\* cited by examiner

TRACER ANALYSIS

CROSS-REFERENCE TO RELATED APPLICATIONS

This application claims priority to U.S. Provisional Patent Application No. 62/878,281, filed on Jul. 24, 2019, the entire contents of which are incorporated herein by reference.

TECHNICAL FIELD

This disclosure relates to the analysis of petroleum reservoirs using tracers.

BACKGROUND

A petroleum reservoir is an underground pool of hydrocarbon compounds contained in porous or fractured rock formations. The petroleum in the reservoir is accessed through one or more borings in the earth that penetrate the material above the reservoir and enable transport of the petroleum to the surface. Water flooding is used, for example, to increase the pressure within the reservoir, thereby increasing oil production rates; and to displace hydrocarbons with the reservoir. Water is ideal for flooding reservoirs due to its ready availability and immiscibility with hydrocarbons. Determining the presence of fluid flow paths between oil wells, and the flow capacity between them, allows for a more detailed description of reservoir heterogeneity and facilitates water flood rate management.

SUMMARY

Cross-well tracers, also referred to as inter-well tracers, can be used to obtain information about reservoir fluid flow patterns by injecting the tracer at an injection location, and subsequently retrieving and analyzing a quantity of the injected tracer at a producing location downstream from the injection location. Tracer test data can be used to validate or update existing reservoir/geological models leading to history matching and production optimization with much greater fidelity.

Nonetheless, despite the advantages associated with using tracer test data for reservoir management, much of the potential of full-field tracer implementation has not yet been realized. One impediment to such implementation is the conventional data collection methodology for breakthrough monitoring, which involves manual collection of samples from each well head, and transportation of the collected samples to a laboratory for work up that typically includes pre-concentration, purification, chemical derivatization (to ensure vaporization and ionizability), and analysis in a gas chromatography triple-quadrupole mass spectrometer (GC-QqQ-MS). Even when an automatic sampler is used to collect the fluids from the producer wells, the vials are still transported manually to the laboratory for work-up.

For modern reservoir management operations, autonomous and near real-time monitoring of full-field tracer campaigns can be accomplished by flow-based optical detection modalities. In these tracer tests, tens or hundreds of uniquely identifiable, optically detectable barcodes are introduced into injector wells and expected to be collected from different producer wells. These tracers are detected at trace/ultra-trace levels and their origins of injection unambiguously determined. By limiting manual intervention in this measurement workflow, some of the major shortcomings of conventional molecular tracers, such as fluorobenzoic acids and naphthalenesulfonic acids, can be overcome. In particular, current measurement methods involving detection of these tracers at ultra-trace levels employ complex and expensive processes carried out by personnel on specialized equipment (GC-QqQ-MS).

To implement this type of tracer detection, this disclosure features methods and systems that can be realized in a flow-through workflow in which a groundwater sample with multiple organic tracer species from a petroleum containing reservoir is separated into multiple components, each of which corresponds to a different tracer species, and then combined with an excess of one or more lanthanide elements, such that the lanthanide element concentration is several times larger than the concentration of the tracer species. In this manner, each lanthanide element will bind to one tracer molecule or no tracer molecules. Washing away or removing unbound lanthanide elements yields a solution in which 1:1 complexes of lanthanide elements and tracer species are present; it has been observed that the limits of detection can be reduced if excess lanthanide ions are removed after tracer-lanthanide binding. Measuring fluorescence emission from such complexes yields a signal which varies approximately linearly with the concentration of the tracer species in the groundwater sample, allowing relative concentrations of each of the multiple organic tracer species to be determined.

In a first aspect, this application features methods that include obtaining a groundwater sample that includes multiple organic tracer species from a petroleum containing reservoir, isolating an aqueous fraction of the groundwater sample, separating the aqueous fraction into a plurality of components, where each component corresponds to a different one of the organic tracer species, combining each of the separated components with at least one lanthanide element to form a plurality of component solutions, where a ratio of the at least one lanthanide element to the separated component in each component solution is 10:1 or greater, and analyzing each component solution to determine a relative amount of each organic tracer species in the groundwater sample.

Embodiments of the methods can include any one or more of the following features.

The multiple organic tracer species can include at least twenty organic tracer species, for example, at least thirty organic tracer species, or at least fifty organic tracer species. The multiple organic tracer species can include 2,6-pyridine dicarboxylic acid. The multiple organic tracer species can include at least one derivative of 2,6-pyridine dicarboxylic acid. The multiple organic tracer species can include 4,7-bis(sulfonatophenyl)-1,10-phenanthroline-2,9-dicarboxylic acid. The multiple organic tracer species can include at least one derivative of 4,7-bis(sulfonatophenyl)-1,10-phenanthroline-2,9-dicarboxylic acid.

Isolating the aqueous fraction of the groundwater sample can include extracting solid material from the groundwater sample. The methods can include extracting the solid material by adsorbing the solid material onto an adsorbent material. The methods can include extracting the solid material by sedimentation.

Isolating the aqueous fraction of the solid material can include removing one or more ionic species from the aqueous fraction. The one or more ionic species can include ions that are complexed by one or more of the multiple organic tracers species. Isolating the aqueous fraction can include reducing an amount of one or more chromogenic species from the aqueous fraction. Isolating the aqueous fraction can include increasing a concentration of at least one of the multiple organic tracer species in the aqueous fraction, relative to a concentration of the at least one species in the groundwater sample.

Separating the aqueous fraction into a plurality of components can include chromatographically separating the multiple organic tracer species. The methods can include measuring retention times of the multiple organic tracers species on a chromatography column, and identifying at least one of the multiple organic tracer species based on its corresponding retention time.

Separating the aqueous fraction into a plurality of components can include performing a first chromatographic separation to separate the aqueous fraction into a first plurality of chromatographic fractions, and performing a second chromatographic separation of at least some members of the first plurality of chromatographic fractions to obtain the plurality of components. At least one of the first and second chromatographic separations can include a reversed-phase chromatographic separation, an ion-exchange chromatographic separation, or a hydrophilic interaction chromatographic separation.

The first chromatographic separation can be performed on a first chromatography column and the second chromatographic separation can be performed on a second chromatography column having a chemical selectivity that differs from a chemical selectivity of the first chromatography column. An output fluid stream from the first chromatography column can be directed into an inlet of the second chromatography column.

Combining each of the separated components with at least one lanthanide element can include, for each component, combining the component with a an aqueous solution that includes the at least one lanthanide element.

The at least one lanthanide element can include two or more lanthanide elements, for example, five or more lanthanide elements. The at least one lanthanide element can include terbium. The at least one lanthanide element can include europium.

At least one of the component solutions can include a complex formed of terbium and 2,6-pyridine dicarboxylic acid or a derivative of 2,6-pyridine dicarboxylic acid. The at least one of the component solutions featuring the complex formed of terbium and 2,6-pyridine dicarboxylic acid or a derivative of 2,6-pyridine dicarboxylic acid can include an ammonium acetate buffer. The ratio of terbium to 2,6-pyridine dicarboxylic acid or a derivative of 2,6-pyridine dicarboxylic acid in the at least one of the component solutions can be 10:1 or greater, for example, 20:1 or greater, 100:1 or greater.

A first component solution can include a complex formed of terbium and a first derivative of 2,6-pyridine dicarboxylic acid, and a second component solution comprises a complex formed of terbium and 2,6-pyridine dicarboxylic acid or a second derivative of 2,6-pyridine dicarboxylic acid different from the first derivative. At least one of the component solutions can include a complex formed of europium and 4,7-bis(sulfonatophenyl)-1,10-phenanthroline-2,9-dicarboxylic acid or a derivative of 4,7-bis(sulfonatophenyl)-1,10-phenanthroline-2,9-dicarboxylic acid. The ratio of europium to 4,7-bis(sulfonatophenyl)-1,10-phenanthroline-2,9-dicarboxylic acid or a derivative of europium to 4,7-bis(sulfonatophenyl)-1,10-phenanthroline-2,9-dicarboxylic acid in the at least one of the component solutions can be 10:1 or greater (for example, 20:1 or greater, 100:1 or greater).

A first component solution can include a complex formed of europium and a first derivative of 4,7-bis(sulfonatophenyl)-1,10-phenanthroline-2,9-dicarboxylic acid, and a second component solution can include a complex formed of europium and 4,7-bis(sulfonatophenyl)-1,10-phenanthroline-2,9-dicarboxylic acid or a second derivative of 4,7-bis(sulfonatophenyl)-1,10-phenanthroline-2,9-dicarboxylic acid different from the first derivative.

The methods can include, prior to analyzing each component solution, purifying each component solution to remove an excess quantity of the at least one lanthanide element from each component solution. The purifying can include, for each component solution, chromatographically separating the excess quantity of the at least one lanthanide element from the organic tracer species of the component solution. The methods can include identifying the organic tracer species of each component solution based on a retention time of each component solution on a chromatography column used to perform the chromatographic separation.

Analyzing each component solution can include measuring a quantity of fluorescence emission from a complex of the organic tracer species of the component solution and one of the at least one lanthanide elements, and determining an estimate of an amount of the organic tracer species in the groundwater sample based on the quantity of fluorescence emission. Measuring the quantity of fluorescence emission can include exposing the component solution to illumination radiation and terminating the exposure at an initial time $t_0$, and at a time $t_m > t_0$, detecting the fluorescence emission from the component solution, where $(t_m - t_0)$ is 2 microseconds or more (for example, 5 microseconds or more). At least one of the component solutions can include a first complex formed by a terbium ion and 2,6-pyridine dicarboxylic acid or a derivative of 2,6-pyridine dicarboxylic acid, and an ammonium acetate buffer solution. At least one of the component solutions can include a second complex formed by a terbium ion and 2,6-pyridine dicarboxylic acid or a derivative of 2,6-pyridine dicarboxylic acid, and an ammonium acetate buffer solution, where the second complex is different from the first complex. At least one of the component solutions can include a first complex formed by a europium ion and 4,7-bis(sulfonatophenyl)-1,10-phenanthroline-2,9-dicarboxylic acid or a derivative of 4,7-bis(sulfonatophenyl)-1,10-phenanthroline-2,9-dicarboxylic acid, and an ammonium acetate buffer solution. At least one of the component solutions can include a second complex formed by a europium ion and 4,7-bis(sulfonatophenyl)-1,10-phenanthroline-2,9-dicarboxylic acid or a derivative of 4,7-bis(sulfonatophenyl)-1,10-phenanthroline-2,9-dicarboxylic acid, and an ammonium acetate buffer solution, where the second complex is different from the first complex. At least one of the component solutions can include a first complex formed by a terbium ion and 2,6-pyridine dicarboxylic acid or a derivative of 2,6-pyridine dicarboxylic acid, and an ammonium acetate buffer solution, and at least one of the component solutions can include a second complex formed by a europium ion and 4,7-bis(sulfonatophenyl)-1,10-phenanthroline-2,9-dicarboxylic acid or a derivative of 4,7-bis(sulfonatophenyl)-1,10-phenanthroline-2,9-dicarboxylic acid, and an ammonium acetate buffer solution.

Embodiments of the methods can also include any of the other features described in this application, including combinations of features described in connection with different embodiments, unless expressly stated otherwise.

In another aspect, this application features systems that include: a purification unit configured to receive a groundwater sample that includes multiple organic tracer species from a petroleum containing reservoir and featuring a solid phase extraction material configured to isolate an aqueous fraction of the groundwater sample; a first chromatographic separation device that includes at least one chromatographic column configured to receive the aqueous fraction and to separate the aqueous fraction into a plurality of components, where each component corresponds to a different one of the organic tracer species; a fluid source coupled to an output of the first chromatographic separation device and configured to combine at least one lanthanide element with each of the separated components; a second chromatographic separation device that includes at least one chromatographic column configured to receive each of the separated components and to separate an excess amount of the at least one lanthanide element from the organic tracer species of each separated component; and an analyzer coupled to an output of the second chromatographic separation device and configured to measure fluorescence emission from complexes of each of the organic tracer species and the at least one of the lanthanide elements, and to determine a relative amount of each organic tracer species in the groundwater sample based on the measured fluorescence emission, where the fluid source is configured to supply the at least one lanthanide element to each of the component solutions so that a ratio of the at least one lanthanide element to the separated component in each component solution is 10:1 or greater.

Embodiments of the systems can include any one or more of the following features.

The multiple organic tracer species can include at least twenty organic tracer species (for example, at least thirty organic tracer species, at least fifty organic tracer species). The multiple organic tracer species can include 2,6-pyridine dicarboxylic acid. The multiple organic tracer species can include at least one derivative of 2,6-pyridine dicarboxylic acid. The multiple organic tracer species can include 4,7-bis(sulfonatophenyl)-1,10-phenanthroline-2,9-dicarboxylic acid. The multiple organic tracer species can include at least one derivative of 4,7-bis(sulfonatophenyl)-1,10-phenanthroline-2,9-dicarboxylic acid.

The purification unit can include a flow through solid phase extraction bed. The purification unit can include an ion-exchange material configured to remove one or more ionic species from the aqueous fraction. The solid phase extraction material can be configured to remove an amount of one or more chromogenic species from the aqueous fraction. A concentration of at least one of the multiple organic tracer species in the aqueous fraction can be increased relative to a concentration of the at least one species in the groundwater sample.

The first chromatographic separation device can include a first chromatography column and a second chromatography column in fluid communication with the first chromatography column, the aqueous fraction can pass through the first chromatography column to generate a first plurality of chromatographic fractions, and at least some members of the first plurality of chromatographic fractions can pass through the second chromatography column to generate the plurality of components. A chemical selectivity of the first chromatography column can be different from a chemical selectivity of the second chromatography column. At least one of the first and second chromatography columns can be a reversed-phase chromatography column. At least one of the first and second chromatography columns can be an ion-exchange chromatography column. At least one of the first and second chromatography columns can be a hydrophilic interaction chromatography column.

The at least one lanthanide element can include two or more lanthanide elements (for example, five or more lanthanide elements).

The fluid source can be configured to supply the at least one lanthanide element so that the ratio of the at least one lanthanide element to the separated component in each component solution can be 20:1 or greater (for example, 100:1 or greater).

The analyzer can include a radiation source, a detector, and a controller connected to the radiation source and to the detector, and configured to analyze each separated component by directing the radiation source to expose the separated component to illumination radiation and terminating the exposure to the illumination radiation at an initial time $t_0$, and measuring fluorescence emission from the separated component at a time $t_m > t_0$, where $(t_m - t_0)$ is 2 microseconds or more. The controller can be configured to determine relative amounts of each organic tracer species in the groundwater sample based on the measured fluorescence emission from the separated components.

Embodiments of the systems can also include any of the other features described in this application, including combinations of features described in connection with different embodiments, except as expressly stated otherwise.

As used in this document, a "derivative" of a chemical substance or moiety is a structurally modified version of that substance or moiety, which contains that substance or moiety as a structural unit. For example, derivatives of a chemical substance or moiety A can include, but are not limited to, substances that include the chemical structure of substance or moiety A functionalized at one or more atoms to include an additional chemical structure (for example, an additional group of one or more atoms). Derivatives of the chemical substance or moiety A can also include chemical substances corresponding to the structure of substance or moiety A with at least one atom removed.

In some embodiments, due to the structural similarity between chemical substance or moiety A and its derivative, both the chemical substance or moiety A and its derivative participate in similar chemical reactions.

Unless otherwise defined, all technical and scientific terms used have the same meaning as commonly understood by one of ordinary skill in the art to which this disclosure belongs. Although methods and materials similar or equivalent to those described can be used in the practice or testing of the present subject matter, suitable methods and materials are described below. All publications, patent applications, patents, and other references mentioned are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description. Other features and advantages will be apparent from the description, drawings, and claims.

DESCRIPTION OF DRAWINGS

Like symbols in the drawings indicate like elements.

DETAILED DESCRIPTION

Introduction

Figure 1:
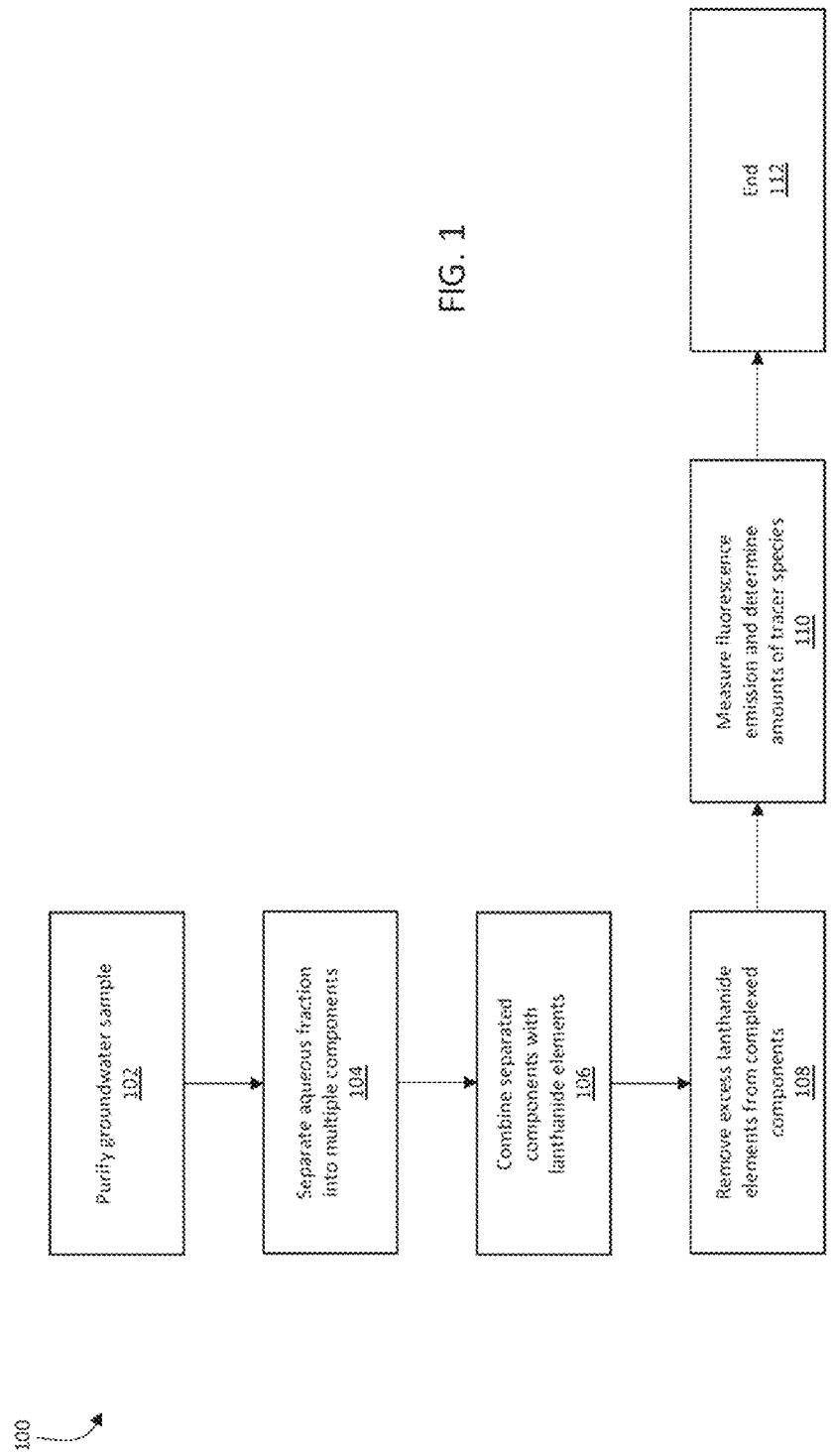
FIG. 1 is a flow chart showing a series of example steps for detecting organic tracer species in a groundwater sample from a petroleum reservoir.

Accurate quantitative detection of the relative amounts of large numbers of organic molecular tracers from groundwater samples taken from a petroleum containing reservoir, particularly over a relatively wide range of possible concentrations, depends in part on the linearity of the measurement signal with respect to the tracer concentration in the groundwater samples. When fluorescence emission from lanthanide-complexed tracers is used as the detection modality, if at least one property of the fluorescence emission—such as instantaneous intensity or time-integrated intensity—scales approximately linearly with tracer concentration, then measurements of fluorescence emission can be used to deduce relative concentrations of organic molecular tracers in groundwater samples. Because such tracers can be reliably distinguished, quantitation of large numbers of different tracers (for example, from many different injector wells) is possible, which allows detailed flow field maps to be constructed for a particular reservoir.

In aqueous solution, certain organic molecular tracers can form a variety of adducts with lanthanide elements. In particular, depending upon factors such as the relative concentrations of the tracers, the lanthanide elements, the presence of interfering ions that may bind to tracer cleft sites, and the solution pH, tracers can form—in addition to 1:1 complexes with lanthanide elements—various multi-coordination complexes in which the lanthanide:tracer ratio is 1:2, 1:3, 1:4, for example. Such multi-coordination complexes affect the linear scaling of fluorescence emission from lanthanide-complexed tracers, thereby making accurate quantitation of the tracers more difficult.

Other factors can also impede quantitation of molecular tracers. For example, free lanthanide ions in solution exhibit detectable fluorescence emission. Further, certain matrix components in groundwater samples (such as polycyclic aromatic hydrocarbons) also exhibit fluorescence emission. These anomalous sources of fluorescence emission can affect measurements of fluorescence emission from complexed molecular tracers, introducing error into quantitative measurements. Still further, certain matrix components of groundwater samples can act either as fluorescence quenchers or enhancers, such that measurements of fluorescence emission even from 1:1 complexed tracers may not scale linearly with tracer concentration.

The methods and systems described in this disclosure include various steps that can be used to reduce or eliminate sources of non-linearity that may affect fluorescence emission measurements from complexed tracer species, and which may therefore interfere with the accurate determination of tracer concentrations in groundwater samples.

Flow field analysis of a petroleum reservoir can be initiated by the injection of multiple organic tracer species at different corresponding injection sites or wells within the reservoir. The organic tracer species propagate through the reservoir according to complex flow patterns. Groundwater samples withdrawn at a producing site or well will typically include concentrations of multiple different organic tracer species corresponding to multiple injection sites. The concentrations of the various tracer species represent information about flow field patterns linking the injection and production sites.

In some embodiments, for example, a groundwater sample can include at least 10 different organic tracer species (such as at least 15 different species, at least 20 different species, at least 25 different species, at least 30 different species, at least 40 different species, at least 50 different species). The methods and systems described can be used to accurately quantify each of these different tracer species, providing a complete multi-dimensional picture of reservoir flow patterns.

Examples of methods for injecting and recovering organic tracer species to and from petroleum reservoirs, and examples of suitable organic tracer species, are described in U.S. Patent Application Publication No. US 2019/0226326, the entire contents of which are incorporated in this disclosure by reference.

Methods for Tracer Analysis

FIG. 1 is a flow chart 100 that shows a series of example steps for analyzing a groundwater sample from a petroleum containing reservoir. After a sample that includes multiple organic tracer species has been obtained from a production site, in a first step 102, the sample is purified to isolate an aqueous fraction of the groundwater sample from other sample components such as dissolved salts and organic matrix components. A variety of methods can be used to purify the sample in step 102. In some embodiments, for example, the sample can be passed over or through a solid phase extraction (SPE) material (for example, by flowing the sample over or through a solid phase extraction bed). The tracer species, certain organic components, and certain other undesired, interfering species are adsorbed onto the solid phase extraction material, while the aqueous phase of the sample (containing the salts and other undesired, interfering species not adsorbed on the SPE materials) flows through the solid phase extraction material. The adsorbed moieties can selectively eluted with a strong solvent (for example, acetonitrile or methanol with or without pH adjustments) after washing the SPE material with aqueous solvent.

Figure 2B:
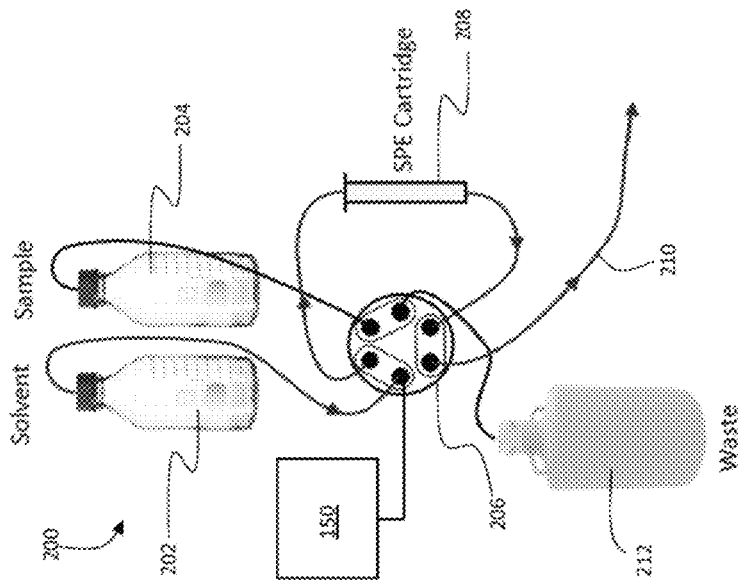
FIGS. 2A and 2B are schematic diagrams of an example of a solid phase extraction purification unit.
Figure 2A:
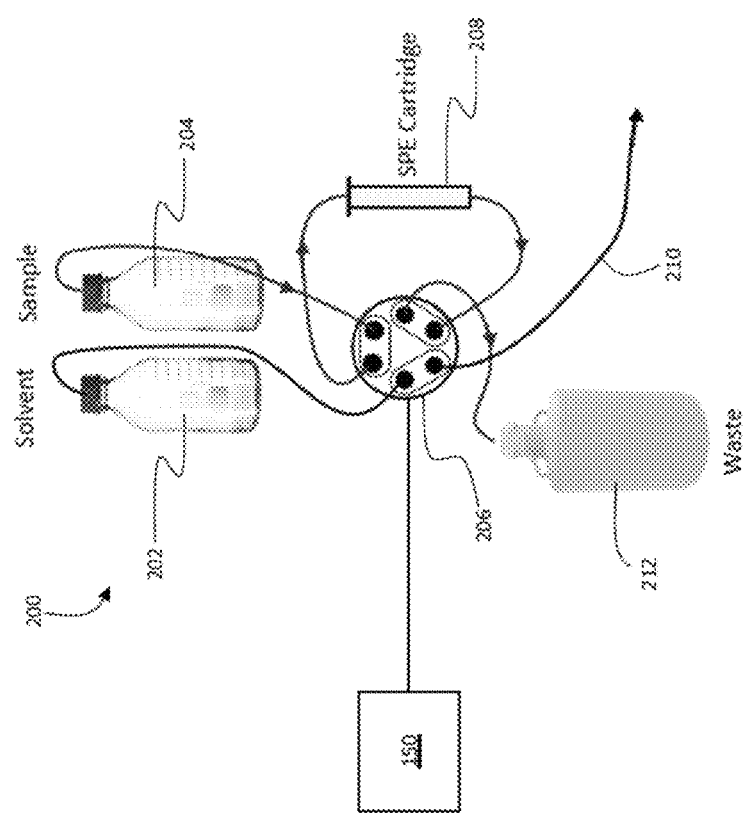

FIGS. 2A and 2B are schematic diagrams showing an example of a purification unit 200 that can be used to purify the groundwater sample. Purification unit 200 can be implemented as an in-line, fully automated solid phase extraction system, with one or more switching valves to load and elute the sample from a SPE bed, with no manual intervention to dispense the sample or solvents. The SPE-DEX 5000 Automated Extraction System (Horizon Technology, Salem, N.H.) and the ASPEC 274 Automated SPE system (Gilson, Middleton, Wis.) are examples of commercially available instruments that can be used as purification unit 200.

Purification unit 200 includes a solvent reservoir 202, a sample reservoir 204, a multi-way valve 206, a SPE bed 208 (implemented as a SPE cartridge or disk, for example), an outlet 210, and a waste container 212. Valve 206 is connected to an electronic controller 150 which regulates the operation of the valve.

During operation, with valve 206 in the first position as shown in FIG. 2A, solvent from solvent reservoir 202 flows directly through outlet 210 and into a first chromatographic separation device that will be discussed further below. The groundwater sample flows directly from sample reservoir 204 onto SPE bed 208. Adsorption of various tracer components in the groundwater sample occurs on the SPE material contained in SPE bed 208, where they are retained.

After the sample has been loaded onto SPE bed 208, controller 150 switches valve 206 to the second position as shown in FIG. 2B. In this position, solvent from solvent reservoir 202 flows through SPE bed 208, eluting tracer species from SPE bed 208. The eluted tracer species flow through outlet 210 to the first chromatographic separation device.

Although purification unit 200 includes only a single solvent reservoir 202 in FIGS. 2A and 2B, more generally purification unit 200 can include multiple solvent reservoirs. For example, purification of different groundwater samples can, in certain circumstances, be improved through the use of a graded sequence of elution solvents, and purification unit 200 can include multiple sample reservoirs to permit a sequence of solvents to flow through SPE bed 208. Purification unit 200 can also include multiple valves, conduits, and other fluid directing components, controlled by controller 150, to allow multiple solvents to be directed through SPE bed 208 in a desired sequence.

Purification unit 200 can also include reservoirs for additional solvents such as wash solvents that can be used during purification of the groundwater sample. As described above, such reservoirs can be connected to SPE bed 208 through valves, conduits, and other fluid directing components under the control of controller 150.

In certain embodiments, purification unit 200 can include multiple SPE beds 208 that include different solid phase extraction media. For example, depending upon the nature of the groundwater sample, it can be advantageous in some circumstances to flow the sample through a sequence of SPE beds, each of which is designed to adsorb and retain specific components from the sample. Different elution conditions (for example, different elution solvents, solvent volumes, and times) can be used for each SPE bed under the control of controller 150. Further, because SPE beds 208 may need to be periodically replaced, by using multiple SPE beds, the beds can be individually replaced at different times as they become saturated.

The solid phase extraction medium is a chemically active stationary phase that functions to retain substances as the groundwater sample is passed over it. Different solid phase extraction media can be used for specific tracer species to yield desired retention times, depending upon the interactions between the tracer molecules and the SPE material, and the elution solvents being used.

Figure 6:
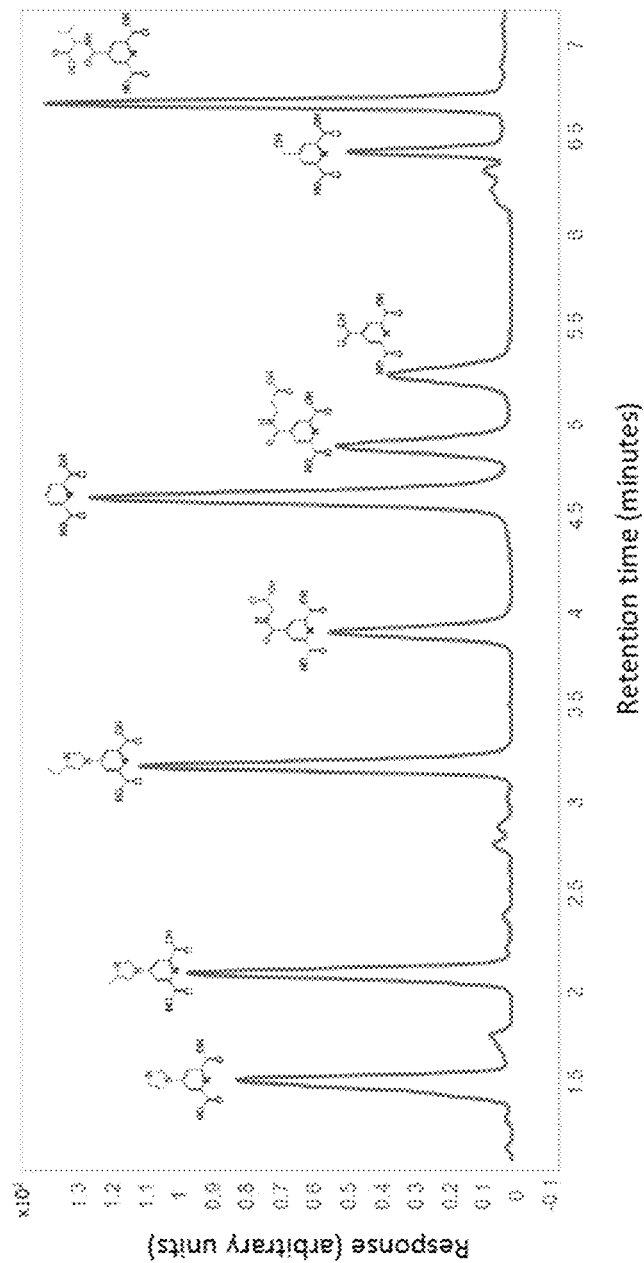
FIG. 6 is a graph showing a liquid chromatogram of nine different DPA-based tracer species in a single solution.

For example, for tracer species corresponding to 2,6-pyridine dicarboxylic acid (DPA) or a derivative of DPA (examples of which are shown in FIG. 6), an ISOLUTE®

ENV+SPE cartridge (available from Biotage, Uppsala, Sweden) which contains a crosslinked, hydroxylated polystyrene-divinylbenzene copolymer can be used. This SPE material can be effectively used for extracting polar analytes from large volume water samples.

In general, a variety of different derivatives of DPA can be used as tracer species. In addition to the examples shown in FIG. 6, suitable derivatives of DPA that can be used as tracers include, but are not limited to, derivatives that include one, two, or three substituents on the pyridine ring. Examples of substituents that can be present include, but are not limited to, linear and branched alkyl groups that include from 1-20 carbon atoms, linear and branched alkenyl groups that include from 1-20 carbon atoms, linear and branched alkynyl groups that include from 1-20 carbon, hydroxyl groups, amino groups, nitro groups, cyclic aliphatic groups that include from 2-20 carbon atoms and can optionally include one or more heteroatoms such as N, O, S, and P, one or more aromatic groups that include from 2-20 carbon atoms and can optionally include one or more heteroatoms such as N, O, S, and P, aliphatic carboxylic acid groups, aromatic carboxylic acid groups, aliphatic amide groups, aromatic amide groups, aliphatic aldehyde groups, aromatic aldehyde groups, aliphatic ketone groups, aromatic ketone groups, aliphatic ether groups, aromatic ether groups, and combinations of any of the foregoing groups (for example, one of the foregoing groups with one or more of the foregoing groups as substituents thereon). Any of the tracer species shown in FIG. 6 can also include combinations of any one or more of the groups described above as substituents.

Figure 3:
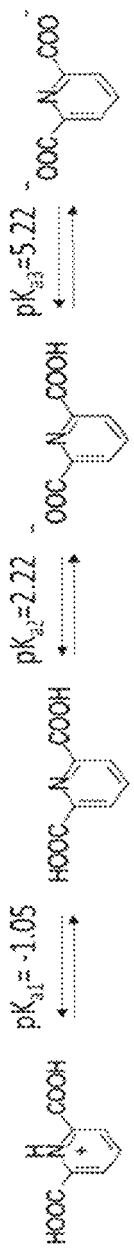
FIG. 3 is a schematic diagram showing different ionization states of 2,6-pyridine dicarboxylic acid (DPA).

The pKa values of DPA are −1.05, 2.22 and 5.22, and the related molecular species are shown in FIG. 3. At low pH values of between 1-2, the DPA molecules exist in a protonated form, which have strong interactions with the polystyrene-divinylbenzene copolymer through hydrophobic and aromatic π-π forces. At neutral or basic pH values, the DPA molecules are in deprotonated form, weaken the interaction with the SPE material, and thus can be selectively washed out by a solvent such as methanol. As an example, pre-concentration and purification of DPA-based tracer species can be performed using the ISOLUTE® ENV+ cartridge with a HCl or $H_3PO_4$ solution at pH<2.2 in a groundwater sample, followed by elution with a small amount of a strong solvent such as methanol or acetonitrile. Depending on the tracer species being eluted, the strong solvent can be pH adjusted with basic compounds, for example, to improve recovery. The molar concentration of a DPA-based tracer species can be enriched by more than 100 times from an initial DPA concentration of 1 part per billion (ppb). Further, typical recovery rates of approximately 95% can be achieved.

Figure 4:
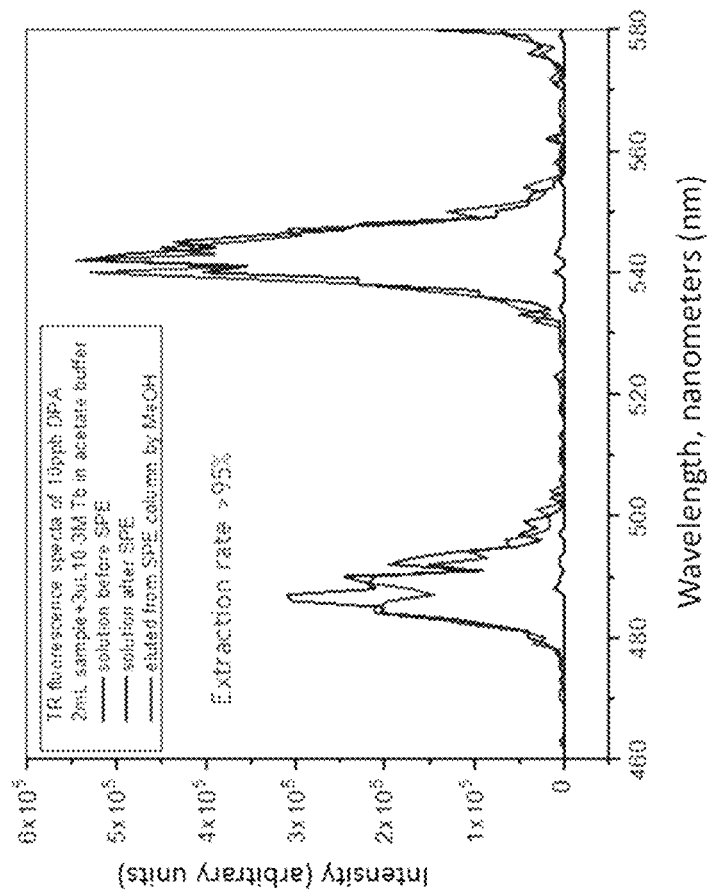
FIG. 4 is a graph showing fluorescence emission measurements for a DPA-based tracer species before and after purification of a groundwater sample using a solid phase extraction material.

FIG. 4 is a graph showing fluorescence emission spectra for a DPA solution with a molar concentration of 10 ppb prior to purification on an ISOLUTE® ENV+ cartridge (using the method described above), and following purification. Comparing the emission spectra, the extraction rate of the DPA tracer species from the SPE material was greater than 95%.

For tracer species based on 4,7-bis(sulfonatophenyl)-1,10-phenanthroline-2,9-dicarboxylic acid (BSPPDA)—that is, BSPPDA and derivatives of BSPPDA—the BSPPDA molecule contains negatively charged sulphonic groups in its structure, which offers good solubility in wide pH range in water but little retention in the non-charged ISOLUTE® ENV+ cartridge.

In general, a variety of different derivatives of BSPPDA can be used as tracer species. Suitable derivatives of BSPPDA that can be used as tracers include, but are not limited to, derivatives that include one, two, three, or four substituents on the phenanthroline ring system. Examples of substituents that can be present include, but are not limited to, linear and branched alkyl groups that include from 1-20 carbon atoms, linear and branched alkenyl groups that include from 1-20 carbon atoms, linear and branched alkynyl groups that include from 1-20 carbon, hydroxyl groups, amino groups, nitro groups, cyclic aliphatic groups that include from 2-20 carbon atoms and can optionally include one or more heteroatoms such as N, O, S, and P, one or more aromatic groups that include from 2-20 carbon atoms and can optionally include one or more heteroatoms such as N, O, S, and P, aliphatic carboxylic acid groups, aromatic carboxylic acid groups, aliphatic amide groups, aromatic amide groups, aliphatic aldehyde groups, aromatic aldehyde groups, aliphatic ketone groups, aromatic ketone groups, aliphatic ether groups, aromatic ether groups, and combinations of any of the foregoing groups (for example, one of the foregoing groups with one or more of the foregoing groups as substituents thereon).

In addition, suitable derivatives of BSPPDA include species in which one or both of the sulfonatophenyl moieties includes any one or more of the above groups, in addition to, or as an alternative to, groups present on the phenanthroline ring system. As discussed above in connection with the phenanthroline ring system, combinations of any of the groups discussed above can be present on one or both of the sulfonatophenyl moieties. If substituted, the sulfonatophenyl moieties can be substituted in the same manner or can be substituted differently.

As an example, for BSPPDA-based tracer species, an anionic exchange type resin, such as CHROMABOND® HR-XAW cartridge or CHROMABOND® HR-XA cartridge (both available from Macherey-Nagel, Dueren, Germany) can be used for purification of the groundwater sample. The CHROMABOND® HR-XAW cartridge contains a solid phase extraction material formed from a polystyrene-divinylbenzene-based copolymer with secondary and tertiary amine groups. The CHROMABOND® HR-XA cartridge contains a solid phase extraction material formed from a polystyrene-divinylbenzene-based copolymer with quaternary ammonium modification. At a pH<6, the quaternary ammonium, secondary and tertiary amine groups of these solid phase extraction resins are protonated to form a positively charged structure, which has strong electrostatic interactions with negatively changed BSPPDA molecules in solution. In addition, the phenanthroline ring in the molecule offers additional interactions with the polystyrene ring structure in the SPE bed through partial hydrophobic and π-π interactions. At neutral or basic conditions, the secondary and tertiary amine groups are deprotonated, weakening the interaction with BSPPDA molecules.

Accordingly, purification of the groundwater sample can be performed under acidic conditions in diluted HCl or $H_3PO_4$ solution at pH<5, preferably pH<2, and then the tracer species can be eluted from the SPE bed with a solvent such as methanol-water at basic pH. An extraction recovery of approximately 85%, starting from an initial solution of BSPPDA in a groundwater sample, at a molar concentration of 1 ppb, has been achieved.

Purifying the groundwater sample by flowing the sample over or through SPE bed 208 performs a number of advantageous functions. As described above, one such function is to separate certain sample matrix components from the organic tracer species of interest. Solid matrix components make flow-through handling of the sample difficult, and elimination of these components reduces contamination of fluidic components.

In addition, certain matrix components may be chromophoric and absorb incident radiation, thereby interfering with fluorescence emission measurements of tracer species. By reducing or eliminating such components from the aqueous fraction, a source of error in the fluorescence emission measurements can be reduced.

In some embodiments, a groundwater sample can include dissolved ions that bind specifically to cleft sites of the tracer species. If binding sites of the tracer species are occupied by these interfering ions, the binding kinetics of complex formation between the tracer species and lanthanide elements can be significantly impaired, and complex formation may even be prevented. By reducing or eliminating these interfering ions from the aqueous fraction, complex formation between tracer species and lanthanide elements (in a subsequent analysis step) is promoted, which yields more accurate quantitative determination of tracer species concentrations.

In certain embodiments, by suitable choice of elution solvent, volume, and time, the concentrations of individual tracer species in the aqueous fraction can be increased relative to their concentrations in the groundwater sample. By increasing the concentrations of tracer species, the species are detected more easily—and with higher accuracy—in fluorescence emission measurements, relative to detection without increasing the concentrations. Because it is the relative concentrations of various tracer species in the groundwater sample that provides information about fluid flow patterns within the reservoir, increasing the concentrations of tracer species in the aqueous fraction by means of solid phase extraction does not impede reservoir management operations.

In some embodiments, other methods can be used in addition to, or as alternatives to, removing matrix substances from groundwater samples using solid phase extraction materials. Such methods can include, for example, sedimentation and selective liquid-liquid extraction.

Returning to FIG. 1, in step 104, the aqueous fraction is separated into a plurality of components. In general, the separation in step 104 is performed in a first chromatographic separation device that includes at least one chromatographic column. For example, in some embodiments, the first chromatographic separation device is a high performance liquid chromatography system, and the components are eluted from the chromatographic column(s) of the first chromatographic separation device during a liquid chromatography separation procedure. Each of the eluted components corresponds to a different one of the organic tracer species present in the aqueous fraction of the groundwater sample that was obtained from step 102.

The separation step 104 effectively accomplishes two important functions. First, separation step 104 separates individual tracer species from one another, allowing the individual species to be identified by retention time. Second, separation step 104 separates other light-absorbing matrix components of the groundwater sample from the tracer species. In general, groundwater samples include a mixture of substances, which includes tracer species and "background" substances. It has been observed that a single chromatographic separation run may not always provide a complete isolation of tracer species from background substances, especially if the matrix contains multiple different dissolved organic matter components (such as, for example, a mixture of different hydrocarbon components). Typically, chromatographic separation of tracer species is implemented by collecting eluted fractions from a chromatographic column during particular time windows. If a background substance co-elutes during a time window associate with a particular tracer species, then the background substance will be present along with the tracer species in the corresponding component solution.

Accordingly, for a particular component solution that nominally corresponds to a single tracer species, it has been observed that fluorescence emission from the solution includes a continuous background signal composed of many overlapping peaks, representing unknown background substances co-eluting along with the tracer species of interest. Examples of such background substances include polycyclic aromatic hydrocarbons and other chromophores. As a result of interference from such background substances, the measured fluorescence emission signal from a particular component solution can be enhanced or quenched by background substances.

Figures 5A, 5B, 5C, 5D:
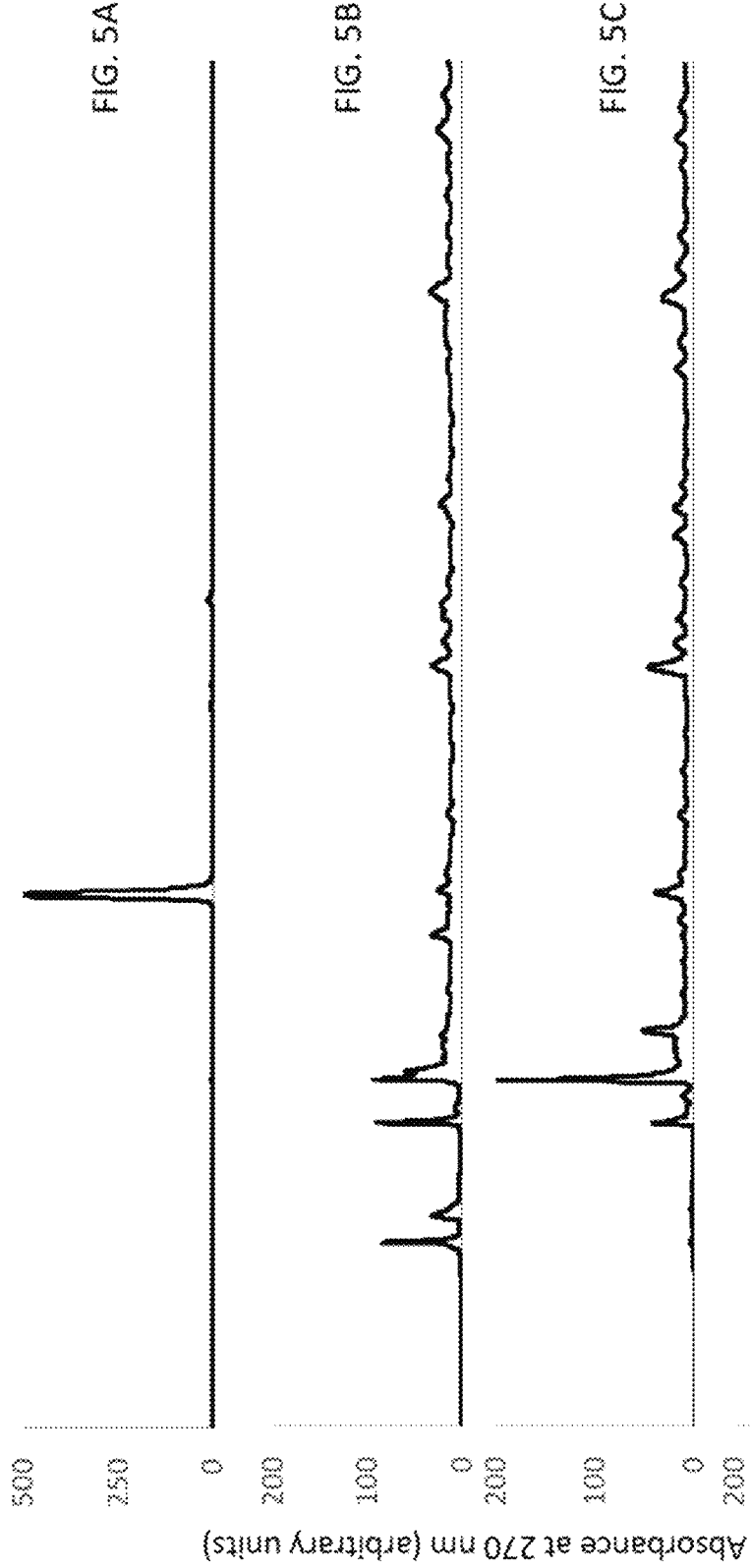
FIG. 5A is a graph showing a liquid chromatogram of a 100 ppm DPA standard solution.
FIGS. 5B and 5C are graphs showing liquid chromatograms of two different groundwater samples.
FIG. 5D is a graph showing a liquid chromatogram of a deionized water sample.

Nonetheless, for a particular tracer species, it is generally observed that most background substances in a raw groundwater sample either can be removed from the matrix by solid phase extraction. Even if some of the background substances do adsorb on the SPE materials, they do not co-elute with the tracer species and can be separated by chromatography. As such, the effect on the fluorescence (or other) signal arising from interference by background substances following separation step 104 is generally a few orders of magnitude less than the effect that would be observed on the fluorescence signal for the raw groundwater sample. FIG. 5A is a liquid chromatogram of a 100 ppm 2,6-pyridine dicarboxylic acid (DPA) standard solution, FIGS. 5B and 5C are liquid chromatograms of two different groundwater samples, and FIG. 5D is a liquid chromatogram of a deionized water sample. The chromatograms in FIGS. 5A-5D represent ultraviolet (UV) absorbance measurements of the samples. Background substances in the groundwater samples can significantly interfere with measurement signals that correspond to a substance of interest (for example, an organic tracer species, as represented by the DPA standard).

Each of the unique organic tracer species in the aqueous fraction that is separated into components in step 104 has a different elution time (or retention time) on the chromatography column. In certain embodiments, these elution times can be measured, and used to uniquely identify the different tracer species corresponding to each component of the aqueous fraction. For example, controller 150 (which can be connected to the first chromatographic separation device, as will be discussed later) can measure the elution times of the components, and correlate or match the elution times with stored reference information to identify the tracer species associated with each component.

In some embodiments, separation step 104 can be performed using a first chromatographic separation device that includes multiple chromatography columns. For example, a two-dimensional (2D) liquid chromatography procedure can be implemented in a first chromatographic separation device that includes two chromatography columns fluidly connected in series so that some components (selective, or "heart cutting" 2D liquid chromatography) or even all components (comprehensive 2D liquid chromatography) of the aqueous fraction that are initially separated by elution from the first chromatography column are then further separated by loading onto, and elution from, the second chromatography column, as they emerge from the first chromatography column. To implement selective 2D liquid chromatography, individual components selected for loading and elution on the second chromatography column are stored in fluid loops and then individually loaded onto the second chromatography column for elution.

More generally, separation step 104 can be performed on a multi-dimensional first chromatographic separation device that includes multiple (for example, two or more, three or more, four or more, five or more, or even more) chromatography columns connected in fluidic series. In some embodiments, each of the multiple chromatography columns has the same chemical selectivity. In certain embodiments, however, at least some of the multiple chromatography columns have different chemical selectivities. Multi-dimensional chromatographic separation procedures are typically implemented to further enhance the separation of organic tracer species from one another, and from background substances in the aqueous fraction.

For example, when the first chromatographic separation device is implemented as a 2D liquid chromatography system with two chromatography columns connected in fluidic series, the chemical selectivities of the two columns can differ. Examples of suitable chemical selectivities for any one or more of the chromatography columns in a multi-dimensional first chromatographic separation device include, but are not limited to, reversed phase, ion-exchange, and hydrophilic interaction.

To demonstrate the separation of a variety of different DPA-based organic tracers using liquid chromatography procedures, a mixture of DPA and eight DPA-based derivatives of DPA was prepared and injected onto a Gemini C18 reversed-phase HPLC column (obtained from Phenomenex, Torrance, Calif.). Separation of the mixture was performed in gradient mode, where the mobile phase was composed of (A) water with 0.3% by volume phosphoric acid, and (B) methanol. The organic component (the percentage of methanol in the mobile phase) was ramped from 10% to 30% by volume over 5.5 minutes, and then stepped up to 40% by volume until 8 minutes.

FIG. 6 is a graph showing a chromatogram of the mixture components separated according to the foregoing procedures. All nine mixture components were separated and readily distinguishable based on their retention times, with a chromatographic peak resolution Rs>1.5.

In some embodiments, the separated components (the tracer species) can be identified based on their retention times in step 104. For example, controller 150 can measure the component retention times (or receive information about the retention times, for example, from a storage device or medium, or from a user interface) and, by comparing the measured retention times to reference information that includes retention times for known tracer species, identify some or all of the separated components from the groundwater sample.

Returning to FIG. 1, after the components (corresponding to individual tracer species) have been separated in step 104, each component is combined with one or more lanthanide elements in step 106 to form lanthanide:tracer complexes. For tracer species that are based on phenanthroline dicarboxylic acid, up to two tracer molecules can coordinate with a single lanthanide ion, and for tracer species that are based on pyridine dicarboxylic acid, up to three tracer molecules can coordinate with a single lanthanide ion.

When multiple tracer molecules bind to a single lanthanide ion, the fluorescence response can be greatly enhanced. However, in general, the largest enhancement occurs generally under lanthanide-starved conditions. For example, significant enhancement for pyridine dicarboxylic acid-based tracer species occurs when the concentration of the tracer species is at least three times in excess of the lanthanide ion concentration. In practice, maintaining this balance of conditions can be challenging. Certain tracer molecules will not contribute to measured fluorescence emission under lanthanide-starved conditions as they will not be complexed to a lanthanide ion. Further, certain lanthanide:tracer complexes will include only a 1:2 or even a 1:1 ratio of lanthanide:tracer. As a result, the measured fluorescence emission signal will include a complex mixture of contributions from lanthanide:tracer adducts of different ratios, and will not include contributions from free tracer molecules. Typically, this measured signal will not scale linearly with tracer species concentrations in the groundwater sample, and may scale substantially non-linearly with tracer species concentration. This unpredictable relationship between the measured fluorescence emission properties and the tracer species concentration makes accurate quantitative determination of the tracer species concentrations difficult.

Another factor that makes maintaining of high tracer:lanthanide concentration ratios challenging is the concentrations of the tracer species in the groundwater sample. In many field measurements, tracer species are present in groundwater samples at concentrations that can be difficult to measure accurately. As a result, maintaining high tracer:lanthanide concentration ratios is impractical for many groundwater samples.

To address the foregoing challenges in step 106, an excess amount of one or more lanthanide elements is added to each component. By using excess lanthanide elements, each lanthanide ion will bind to either 1 or 0 tracer molecules. Furthermore, the lanthanide:tracer binding kinetics will be favored, such that all (or nearly all) of the tracer molecules will bind to a lanthanide ion. Accordingly, even though the overall fluorescence emission intensity is lower relative to the situation described above in which the tracer:lanthanide molar ratio is greater, the fluorescence emission intensity for each component scales approximately linearly with the amount of the corresponding tracer species in the groundwater sample, so that relative amounts (or concentrations) of each tracer species can be accurately determined.

In some embodiments, for example, one or more lanthanide elements are combined with each of the separated components from step 104 so that in each component solution, a molar ratio of the one or more lanthanide elements to the component (organic tracer species) is 5:1 or more (for example, 10:1 or more, 20:1 or more, 30:1 or more, 50:1 or more, 70:1 or more, 100:1 or more, 150:1 or more, 200:1 or more, 300:1 or more).

The lanthanide elements that are combined with the separated components from step 104 can generally include any of the elements in the lanthanide series. Examples of such elements include terbium, europium, cerium, praseodymium, neodymium, promethium, samarium, gadolinium, dysprosium, holmium, erbium, thulium, ytterbium, and lutetium.

In certain embodiments, a single type of lanthanide element is combined with each of the separated components. In some embodiments, however, more than one type of lanthanide element is combined with the separated components. A first lanthanide element can be combined with some of the separated components, while a second lanthanide element can be combined with other separated components. In general, any number of lanthanide elements (for example, two or more, three or more, four or more, five or more, six or more, eight or more) can be combined with the components separated in step 104.

After lanthanide:tracer complexes have been formed in step 106, excess unbound lanthanide elements are removed in step 108. In general, step 108 is performed by a second chromatographic separation device, which can include one or more chromatography columns as will be described further below.

Free lanthanide ions generate measurable fluorescence emission, and although the emission is significantly weaker than the fluorescence emission from lanthanide:tracer complexes, spectral interference from free lanthanide emission can nonetheless affect the accurate quantitative measurement of tracer species in groundwater samples. In effect, fluorescence emission from free lanthanide ions sets up a noise floor for the limit of detection (LOD) for tracer species at trace and ultra-trace concentrations.

Improving the LOD involves reducing the noise floor (contributions to the measured tracer signals arising from free lanthanide ions in the component solutions). In turn, reducing the noise floor due to free lanthanide ions can be accomplished by separating free lanthanide ions from the components (organic tracer species) in the component solutions by performing a liquid chromatographic separation using the second chromatographic separation device.

As an example, separation of free terbium ions from Tb:DPA was performed using hydrophilic interaction liquid chromatography (HILIC). To maintain the stability of Tb:DPA complexes, a buffered ammonium acetate solution (200 millimoles per Liter (mM), pH 5.6) was used as the mobile phase, employing acetonitrile as the organic modifier. Separations were performed using 55% acetonitrile at 30° C. and 1 mL/min flow rate.

Three types of stationary phase functionalities were evaluated and compared for their separation performance: (a) bare silica, (b) poly-hydroxy fructan, and (c) zwitterionic. All of these columns were obtained from Agilent Technologies, as the Poroshell 120 HILIC, Poroshell HILIC-OH5, and Poroshell 120 HILIC-Z columns, respectively.

To detect DPA:Tb complexes, an inline fluorimeter was coupled to the column output. The fluorimeter provided illumination radiation at a wavelength of 270 nanometers (nm), and measured fluorescence emission at 540 nm. Free Tb ions were detected by measuring UV absorption at an illumination wavelength of 230 nm.

Figure 7A:
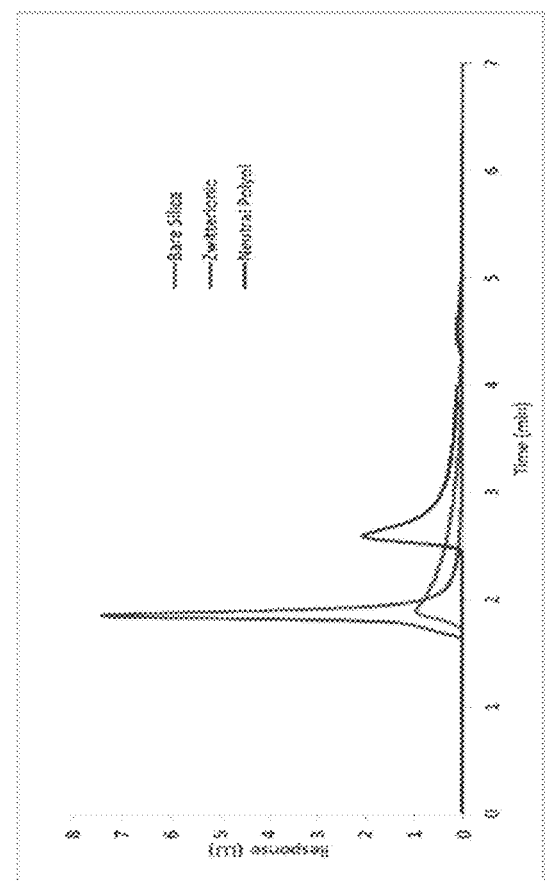
FIG. 7A is a graph showing liquid chromatograms of a DPA:Tb complex eluted on chromatography columns with bare silica, zwitterionic, and neutral polyol stationary phases.

FIG. 7A is a graph showing fluorescence emission as a function of time for the eluent of each of the three different types of columns. The bare silica stationary phase yielded a short retention time with substantial tailing of the Tb:DPA complex peak, indicating that multiple interaction mechanisms likely contributed to the complex's retention on the column. The poly-hydroxy fructan stationary phase yielded a longer retention time with moderate peak tailing, and the zwitterionic phase exhibited the sharpest peak and shortest retention time.

Figure 7B:
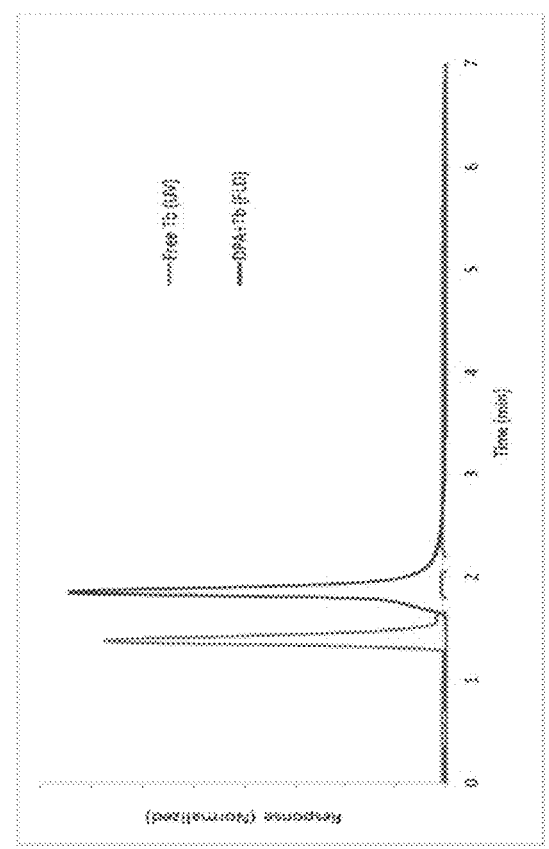
FIG. 7B is a graph showing absorbance of free Tb ions as a function of retention time on a liquid chromatography column with a zwitterionic stationary phase.

FIG. 7B is a graph showing absorbance as a function of time for the eluent from the zwitterionic column. As is evident, each of the three columns was effective in separating the Tb:DPA complexes from free Tb ions, which eluted in the void volume (at earlier times than the Tb:DPA complexes for each type of column).

As discussed above in connection with step 104, the separation operation implemented in step 108 can be a one-dimensional or multi-dimensional chromatographic separation, and the second chromatographic separation device can include one or more chromatographic columns. Combinations of any one or more of the different types of columns and chemical sensitivities can be used in the second chromatographic separation device. Where the device includes multiple columns, the multiple columns can be connected in fluidic series, and some or all of the fractions that elute from an earlier column in the series can be loaded onto and eluted onto later columns in the series. In particular, for workflows in which multiple different types of lanthanide ions are used to complex different tracer species, multi-dimensional chromatographic separations may be advantageous (but are not required) to separate all of the different types of free lanthanide ions from the complexed tracer species.

Returning to FIG. 1, step 108 yields a plurality of component solutions, each of which nominally includes only one tracer species, and which has a molar concentration of each of the different lanthanide elements used to complex the tracer species that is typically in the parts-per-billion or parts-per-trillion range, or even lower. Each of the component solutions is then analyzed in step 110 to determine a relative amount or concentration of each tracer species in the groundwater sample.

A variety of different methods can be used to analyze the complexed tracer species. In some embodiments, for example, fluorescence emission (measured by an analyzer that receives each of the component solutions in a flow-through manner from the second chromatographic separation device) is used for detection. Alternatively, in certain embodiments, absorption measurements (for example, ultraviolet (UV) absorption, measured in a flow-through manner) is used for detection. As another alternative, in some embodiments, eluted components are identified by mass spectrometry.

In some embodiments, non-gated fluorescence or other measurements are performed in which each component solution is illuminated with incident radiation and fluorescence emission, absorption, or another quantity is measured (either a peak measurement or an integrated measurement) over a relatively wide temporal window that includes the time at which illumination occurs.

In certain embodiments, time-gated fluorescence measurements are performed. Aspects of such measurements are described in detail in U.S. Patent Application Publication No. US 2019/0226326. Following flash excitation to illuminate a component solution with incident radiation—a process that ends at a time $t_0$—the lanthanide:tracer complexes has a relatively long excited state lifetime. For example, in some embodiments, a complex's luminescence occurs for a time period greater than 5 microseconds (for example, greater than 8 microseconds, greater than 10 microseconds, greater than 15 microseconds, greater than 20 microseconds, greater than 30 microseconds, greater than 40 microseconds, greater than 50 microseconds, greater than 100 microseconds, greater than 200 microseconds, greater than 500 microseconds, greater than 1 millisecond (ms), greater than 2 ms, greater than 5 ms, greater than 10 ms) after excitation is complete.

Without wishing to be bound by theory, it is believed that the long excited state lifetime occurs due to parity-forbidden transitions between lanthanide ion excited and ground states, which occur more slowly than parity-allowed state-to-state transitions during excitation and further, more slowly than background fluorescence arising from parity allowed excited-to-ground state transitions among other substances that may be present in a component solution. When a lanthanide ion is in close proximity to a sensitizing chromophore (such as a tracer molecule) that either has a strong dipole moment or is anionic such that it can associate ionically with the lanthanide ion, significant enhancement of the lanthanide ion luminescence occurs because the sensitization process circumvents the LaPorte selection rules that normally forbid f-f transitions.

Accordingly, the difference in time scales separates fluorescence or luminescence signals from the lanthanide:tracer complexes (which occur at later times) from fluorescence signals due to other substances that may be present in the component solutions ("background" fluorescence). The difference in excited state lifetimes and concomitant difference in the temporal evolution of emission from the lanthanide: tracer complexes and background substances allows gating of the optical detector such that the detector can be used to measure luminescence from the complex alone, after fluorescence from background substances in the component solution has decayed.

Specifically, by exposing each component solution to incident radiation and terminating the exposure at an initial time $t_0$, and then measuring fluorescence emission beginning at a later time $t_m$, the measured fluorescence emission signal—when $(t_0-t_m)$ is chosen appropriately—can correspond nearly entirely to fluorescence emission from lanthanide:tracer complexes.

In general, it has been found that by choosing $(t_0-t_m)$ to be 2 microseconds or more (2.5 microseconds or more, 3 microseconds or more, 3.5 microseconds or more, 4 microseconds or more, 4.5 microseconds or more, 5 microseconds or more), the measured fluorescence emission signal contains contributions from only the lanthanide:tracer complexes in component solutions, without measurable interference from lanthanide luminescence.

After fluorescence emission has been measured in step 110, a controller (for example, controller 150) determines relative amounts or concentrations of each of the tracer species in the groundwater samples based on the measurements. For example, calibration information (such as a calibration curve) or stored reference information can be used to convert measurements of gated, time-integrated fluorescence intensity for each tracer species to relative quantities or concentration values for the tracer species. The relative quantities or concentration values can then optionally be used by controller 150 (or another processing unit) to execute a variety of reservoir reporting and management operations.

Relative quantities or concentration values can be determined from fluorescence or other measurements in various ways. In some embodiments, peak areas (that is, the area under each peak) are used to calculated relative quantities or concentrations of each tracer species. To convert these relative quantities or concentrations to absolute values, reference information (in the form of previously measured concentration values or a calibration curve) is used. For example, a calibration curve can be determined by measuring fluorescence emission or other signals for solutions with known concentrations of tracer species, so that peak area is determined as a function of known concentration for each tracer species of interest. By establishing a functional relationship between peak area and concentration (for example, by regression analysis) for each tracer species, a calibration curve is generated. Subsequently, measured peak areas for solutions of unknown tracer species concentration can be used to determine absolute tracer species concentration values using the calibration curve.

The procedure shown in FIG. 1 then ends at step 112.
Attributes Affecting Separation and Detection of Tracers
  (i) Solvent and Buffer It has been determined that the nature of the solvent (including the solvent's buffered pH) may play an important role in ensuring that fluorescence emission measurements of the component solutions can be used to accurately determine relative amounts or concentrations of tracer species in a groundwater sample. To investigate the role of the solvent, fluorescence emission measurements were performed in 1.0 mol/L (M) bioluminescence grade sodium acetate buffer (pH adjusted with 1.0 M acetic acid to pH ~5.6), and in 1.0 M HPLC-grade ammonium acetate (pH adjusted with 1.0 M acetic acid to pH ~5.7) to evaluate the background fluorescence intensity against fluorescence emission from a trace amount of a molecular tracer species (molar concentration of 100 parts per trillion (ppt) of BSPPDA, and molar concentration of 1 ppb of DPA). Lanthanide ion concentrations were varied between $5\times10^{-6}$ M and $5\times10^{-8}$ M for europium ions in the analysis with BSPPDA, and between $5\times10^{-6}$ M and $1\times10^{-7}$ M for terbium in the analysis with DPA.

Figure 8A:
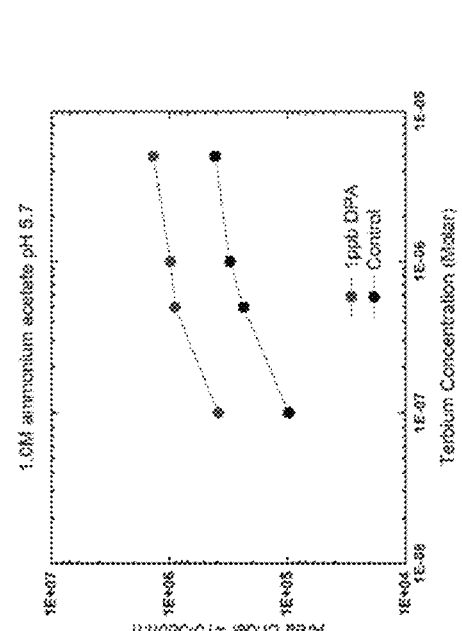
FIG. 8A is a graph showing measurements of fluorescence intensity for a solution having a molar concentration of 1 ppb of DPA in 1.0 M sodium acetate at pH 5.6, as a function of terbium ion concentration.
Figure 8B:
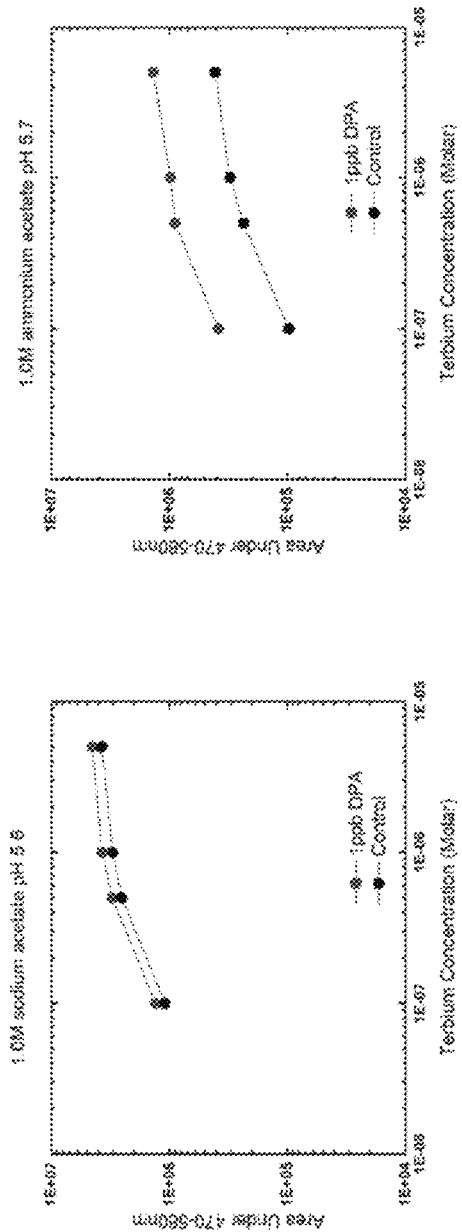
FIG. 8B is a graph showing measurements of fluorescence intensity for a solution having a molar concentration of 1 ppb of DPA in 1.0 M ammonium acetate at pH 5.7, as function of terbium ion concentration.

FIG. 8A is a graph showing measurements of fluorescence intensity for a solution with a molar concentration of 1 ppb of DPA in 1.0 M sodium acetate at pH 5.6, as a function of terbium ion concentration, and measurements of fluorescence emission from a control solution (with terbium ions only and no DPA) are also shown. FIG. 8B is a graph showing measurements of fluorescence intensity for a solution having a molar concentration of 1 ppb of DPA in 1.0 M ammonium acetate at pH 5.7, as function of terbium ion concentration, and measurements of fluorescence emission from a control solution (with terbium ions only and no DPA) are also shown.

Figure 8C:
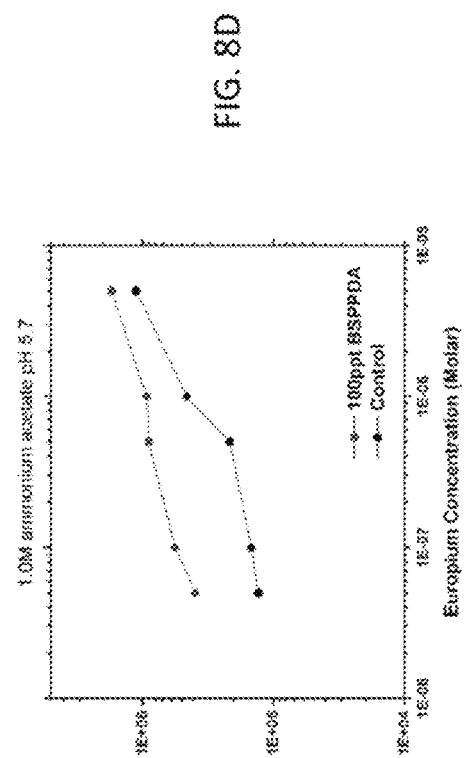
FIG. 8C is a graph showing measurements of fluorescence intensity for a solution having a molar concentration of 100 ppt of BSPPDA in 1.0 M sodium acetate at pH 5.6, as a function of europium ion concentration.
Figure 8D:
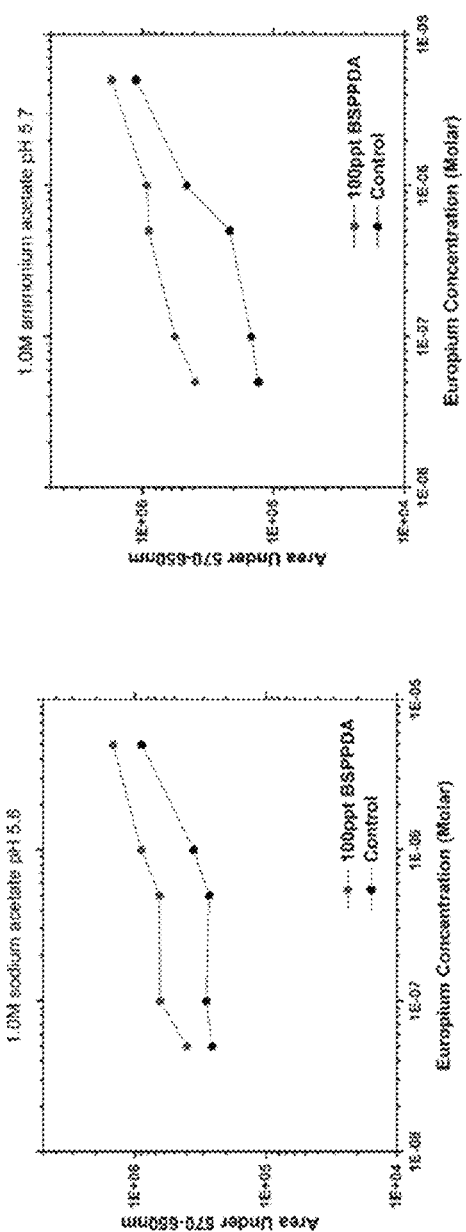
FIG. 8D is a graph showing measurements of fluorescence intensity for a solution having a molar concentration of 100 ppt of BSPPDA in 1.0 M ammonium acetate at pH 5.7, as a function of europium ion concentration.

Similarly, FIG. 8C is a graph showing measurements of fluorescence intensity for a solution having a molar concentration of 100 ppt of BSPPDA in 1.0 sodium acetate at pH 5.6, as a function of terbium ion concentration, along with fluorescence emission measurements from a corresponding control solution, and FIG. 8D is a graph showing measurements of fluorescence intensity for a solution having a molar concentration of 100 ppt of BSPPDA in 1.0 M ammonium acetate at pH 5.7, as a function of terbium ion concentration, along with fluorescence emission measurements from a corresponding control solution.

Various literature sources (see, for example, Hindle et al., "Dipicolinic acid (DPA) assay revisited and appraised for spore detection," Analyst 124: 1599-1604 (1999)), have reported that sodium acetate buffer is preferred for stabilizing the fluorescence of lanthanide ions bound at a 1:1 ratio to sensitizing ligands (such as the tracer species), because they effectively exclude water from complexing the lanthanide ions, thereby ensuring that the ions remain complexed by the tracer species.

However, the measurements shown in FIGS. 8A-8D demonstrate a greater signal-to-noise ratio across the concentrations of terbium and europium ions tested in ammonium acetate solution rather than sodium acetate solution. This result indicates that the choice of acetate solution to lower the background signal (and improve the limit of detection) could be lanthanide ion dependent. The choice of solution in which to perform quantification analysis by fluorescence is important because by increasing the signal-to-noise ratio in fluorescence emission measurements for the lanthanide: tracer complexes can help to eliminate false positive measurements in an automated work flow.

Figure 9A:
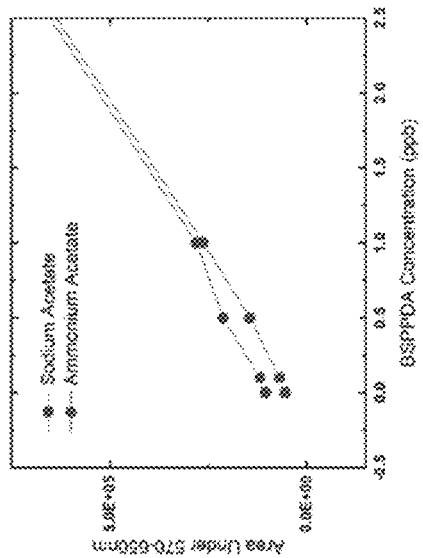
FIG. 9A is a graph showing fluorescence intensity measurements for BSPPDA:Eu complexes, with Eu concentration held constant at $10^{-7}$ and the BSPPDA concentration varying in solution, in both sodium acetate and ammonium acetate solvents.
Figure 9B:
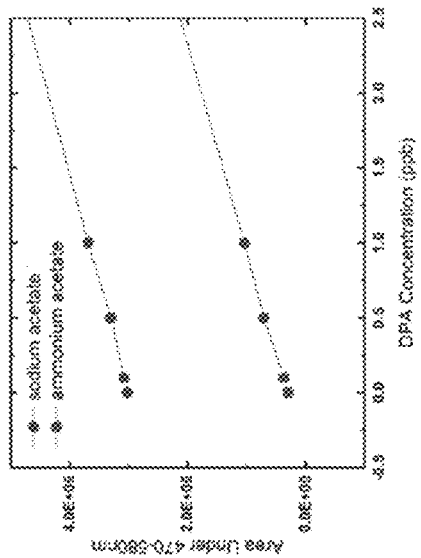
FIG. 9B is a graph showing an enlarged view of a portion of the graph in FIG. 9A.
Figure 9C:
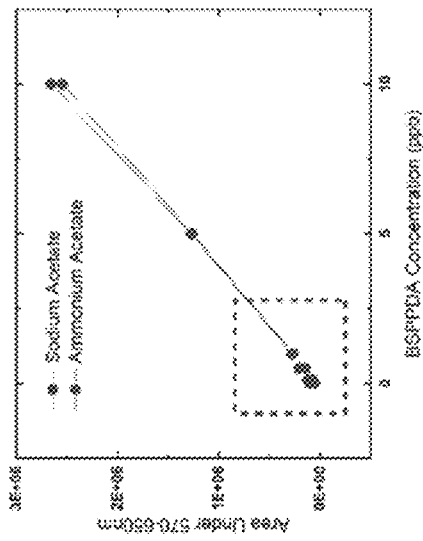
FIG. 9C is a graph showing fluorescence intensity measurements for DPA:Tb complexes, with Tb concentration held constant at $10^{-6}$ and the DPA concentration varying in solution, in both sodium acetate and ammonium acetate solvents.
Figure 9D:
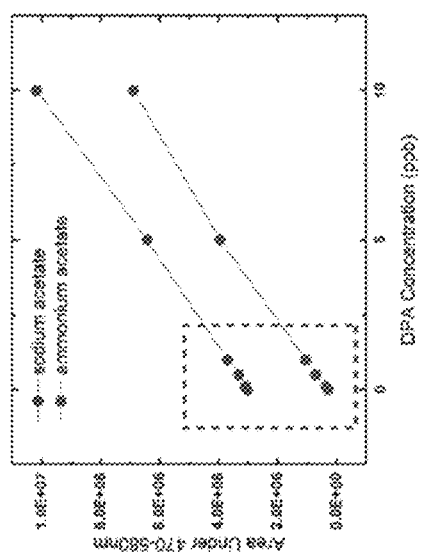
FIG. 9D is a graph showing an enlarged view of a portion of the graph in FIG. 9C.

The effect of the solvent's buffered pH on the linearity of the fluorescence emission response was also investigated with tracer molecules at trace and ultra-trace concentration levels. Lanthanide ion concentrations were maintained constant ($1\times10^{-7}$ M for europium and $1\times10^{-6}$ M for terbium), and fluorescence emission measurements were performed in 1.0 M ammonium acetate and 1.0 M sodium acetate solutions. FIG. 9A is a graph showing fluorescence intensity measurements for BSPPDA:Eu complexes, with Eu concentration held constant and the BSPPDA concentration varying in solution, in both sodium acetate and ammonium acetate solvents. FIG. 9B shows an enlarged portion of the graph in FIG. 9A (indicated by the dashed box in FIG. 9A). FIG. 9C is a graph showing fluorescence intensity measurements for DPA:Tb complexes, with Tb concentration held constant and the DPA concentration varying in solution, in both sodium acetate and ammonium acetate solvents. FIG. 9D shows an enlarged portion of the graph in FIG. 9C (indicated by the dashed box in FIG. 9C).

In FIGS. 9A and 9B, non-linearity of the measured fluorescence emission was observed at molar BSPPDA concentrations between 100 ppt and 1 ppb for BSPPDA:Eu complexes in sodium acetate solution; non-linearity of the measured fluorescence emission was not observed for BSPPDA:Eu complexes in ammonium acetate. Further, no non-linearity was observed in the measured fluorescence emission for DPA:Tb complexes in either sodium acetate or ammonium acetate solvents. These results indicated that for certain tracer:lanthanide complexes, 1.0 M ammonium acetate solution may provide a more stable matrix for fluorescence measurements than the conventionally reported sodium acetate matrix.

The compatibility of the solvent buffer solution used to introduce lanthanide species with the chromatography mobile phase can also affect the measured fluorescence emission. The mobile phase in reversed-phase chromatography system typically consists of a mixture of aqueous and organic solvents, of which acetonitrile is a common choice, and is acidified to approximately pH 2. As discussed above, to realize improved fluorescence emission from tracer:lanthanide complexes, the solvent mixture generally includes a relatively high concentration of acetate ions, which displace water molecules from the lanthanide ion so that the lanthanide luminescence is not quenched by O—H vibration of the coordinated water molecules. In addition, the solvent mixture typically has a pH of between approximately 5 and 6.

Static experiments showed that a 1 M sodium acetate buffer is miscible with up to 30% (by volume) acetonitrile. Using a crystal violet indicator to determine miscibility (which has high solubility in acetonitrile and moderate solubility in sodium acetate buffer), a phase separation was observed once the acetonitrile content exceeded 30% by volume, although no precipitation was visible.

In some embodiments, the mobile chromatography phases used in the methods described herein can include acetate ions at concentrations of between 0.5 M and 3.0 M (for example, between 0.5 M and 2.8 M, between 0.5 M and 2.6 M, between 0.5 M and 2.4 M, 0.5 M and 2.2 M, between 0.5 M and 2.0 M, between 0.5 M and 1.8 M, between 0.5 M and 1.6 M, between 0.5 M and 1.5 M, between 0.7 M and 3.0 M, between 0.7 M and 2.8 M, between 0.7 M and 2.6 M, between 0.7 M and 2.4 M, between 0.7 M and 2.2 M, between 0.7 M and 2.0 M, between 0.9 M and 3.0 M, between 0.9 M and 2.8 M, between 0.9 M and 2.6 M, between 0.9 M and 2.4 M, between 0.9 M and 2.4 M, between 0.9 M and 2.2 M, between 0.9 M and 2.0 M, or any other range between 0.5 M and 3.0 M).

In certain embodiments, in any of the mobile chromatography phases described above, acetonitrile can be present at a concentration of between 0% and 30% (for example, between 2% and 30%, between 4% and 30%, between 6% and 30%, between 8% and 30%, between 10% and 30%, between 12% and 30%, between 14% and 30%, between 16% and 30%, between 18% and 30%, between 20% and 30%, between 25% and 30%, or any other range between 0% and 30%).

In addition to acetonitrile, the chromatography methods used for quantifying lanthanide tracers typically also include phosphoric acid to acidify the aqueous component, which protonates the carboxylic acid groups in the tracer ligands and promotes retention on the chromatography column.

The compatibility of phosphoric acid with the in-line mixed lanthanide solution was investigated in connection with the methods described in this disclosure. The strong binding of the phosphate anion to a lanthanide ion is known to quench its fluorescence intensity. This would have a detrimental effect on inline detection, since the mobile phase from the chromatography column(s) is typically mixed directly with the lanthanide solution prior to detection.

Figure 16:
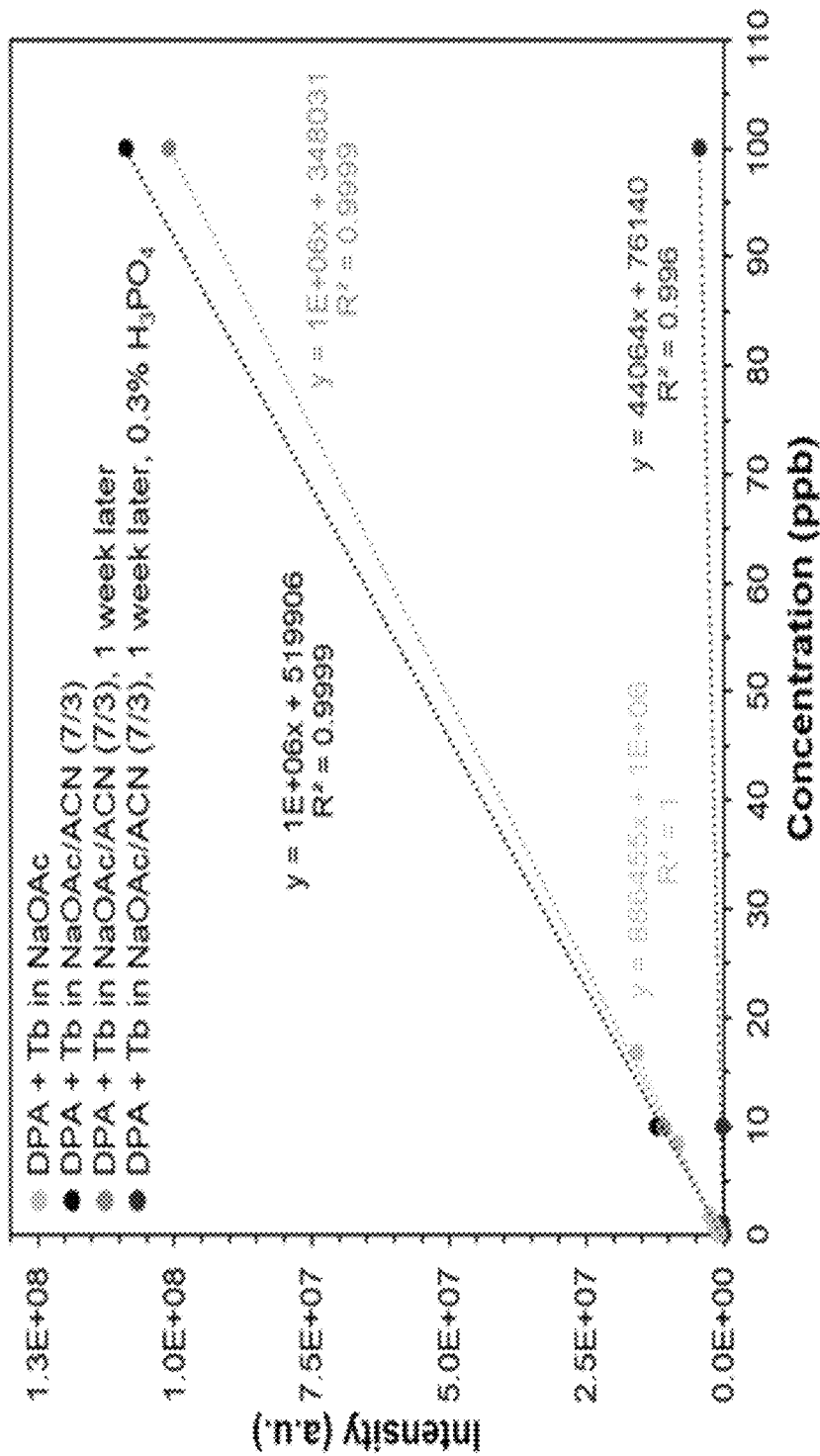
FIG. 16 is a graph showing measured fluorescence intensity as a function of DPA concentration in for a series of DPA samples under different solvent conditions.

To assess the effect of phosphoric acid on fluorescence emission measurements, a static fluorescence experiment was carried out using dipicolinic acid (DPA) as a model tracer to investigate the effects of both acetonitrile and phosphoric acid on the fluorescence intensity. FIG. 16 shows fluorescence emission intensity as a function of tracer concentration under a variety of different solution conditions. The presence of up to 30% acetonitrile in solution did not significantly reduce fluorescence emission intensity, even after 1 week. In contrast, the presence of 0.3% phosphoric acid resulted in a significant decrease of more than one order of magnitude in the fluorescence emission intensity.

As an alternative to phosphoric acid, other acids can also be used to acidify the mobile chromatography phase. For example, acids commonly used in reversed-phase chromatography are acetic acid, formic acid, and trifluoroacetic acid (TFA). Acetic acid and formic acid were previously determined to be too weak to achieve a mobile phase pH of 2-3, so TFA was selected as an alternative. The same static experiment described above was carried out using 0.1% and 0.5% (by volume) TFA in a sodium acetate buffer containing $10^{-6}$ M $TbCl_3$.

Figure 17:
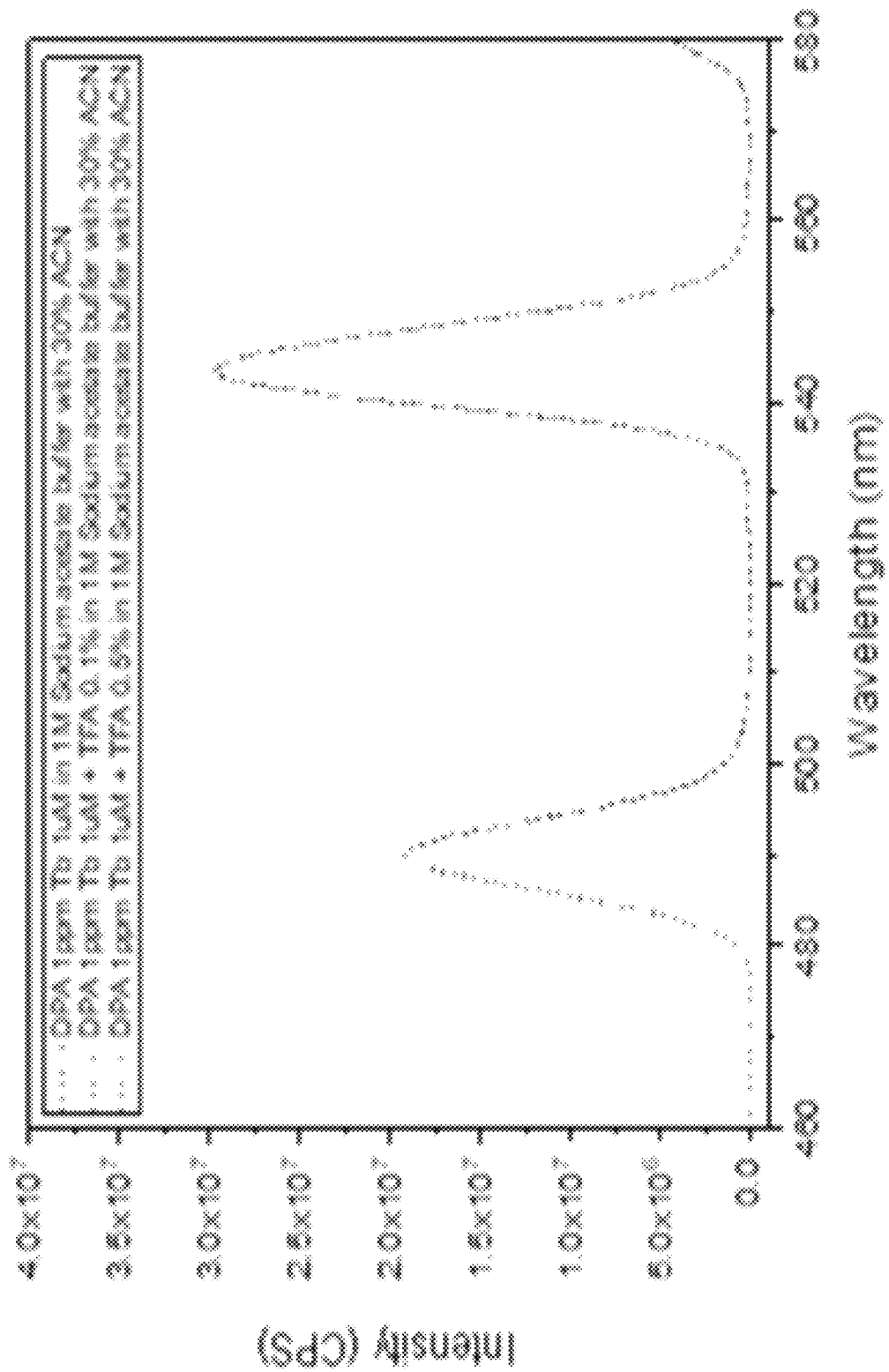
FIG. 17 is a graph showing measured fluorescence spectra for a series of DPA samples in acetate buffer with different concentrations of trifluoroacetic acid.

FIG. 17 shows fluorescence emission spectra for three solution mixtures with no TFA, with 0.1% by volume TFA, and with 0.5% by volume TFA. Each solution mixture contained 30% by volume acetonitrile in a 1 M sodium acetate buffer. As shown in FIG. 17, no significant different in fluorescence emission intensity was observed, demonstrating that TFA is suitable for acidifying mobile chromatography phases without appreciably quenching tracer fluorescence emission.

In general, in any of the solution mixtures described herein that are used to measure fluorescence intensity of tracer complexes, the volumetric concentration of TFA can be between 0.1% and 3.0% (for example, between 0.1% and 2.8%, between 0.1% and 2.6%, between 0.1% and 2.4%, between 0.1% and 2.2%, between 0.1% and 2.0%, between 0.1% and 1.8%, between 0.1% and 1.6%, between 0.1% and 1.4%, between 0.1% and 1.2%, between 0.1% and 1.0%, between 0.1% and 0.8%, between 0.1% and 0.6%, between 0.1% and 0.5%, between 0.2% and 3.0%, between 0.2% and 2.5%, between 0.2% and 2.0%, between 0.2% and 1.5%, between 0.2% and 1.0%, between 0.2% and 0.5%, between 0.3% and 3.0%, between 0.3% and 2.5%, between 0.3% and 2.0%, between 0.3% and 1.5%, between 0.3% and 1.0%, between 0.3% and 0.5%, between 0.4% and 3.0%, between 0.4% and 2.5%, between 0.4% and 2.0%, between 0.4% and 1.5%, between 0.4% and 1.0%, between 0.4% and 0.5%, or any other range between 0.1% and 3.0%).

Buffer composition was also investigated to determine its effect on fluorescence measurement sensitivity. A series of static experiments was carried out comparing the sodium acetate buffer at pH 5.6 with (4-(2-hydroxyethyl)-1-piperazineethanesulfonic acid) (HEPES) buffers at pH 6.5 and 7.3. For each buffer solution, fluorescence emission intensity (integrated area under fluorescence emission peak) was determined as a function of DPA concentration for a Tb:DPA complex.

Figure 18C:
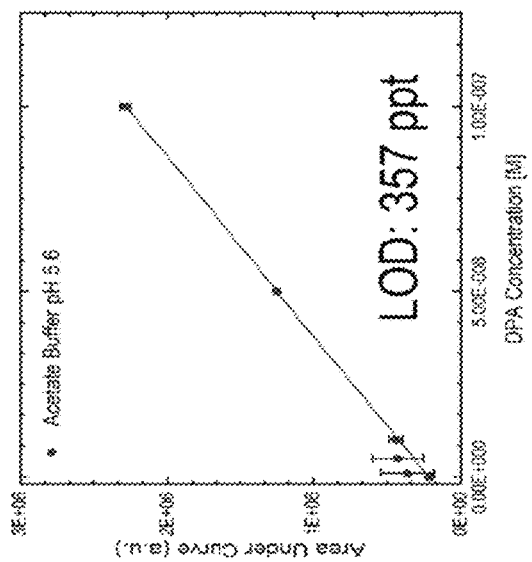
FIGS. 18A-18C are graphs showing measured fluorescence signals from DPA samples in different buffer solutions.
Figure 18B:
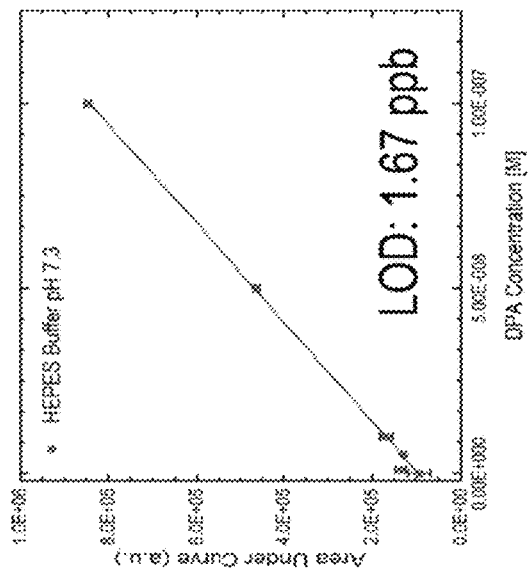
Figure 18A:
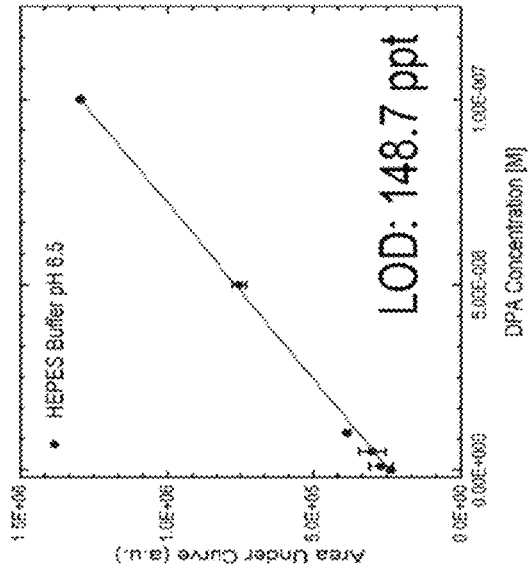

FIGS. 18A-18C show measured fluorescence emission for the HEPES buffer at pH 6.5, the HEPES buffer at pH 7.3, and the sodium acetate buffer at pH 5.6, respectively. At lower DPA concentrations (100 ppt to 1 ppb), the errors bars for the sodium acetate buffer were large, indicating a high variability of sensitivity. However, the slope of the sodium acetate curve was largest, suggesting that the dynamic range for the sodium acetate buffer was better than for either HEPES buffer. While the calculated limit of detection (LOD) for the sodium acetate buffer was low, it is important to make sure that blank samples are stable to take advantage of this high sensitivity.

The measurements shown in FIGS. 18A-18C suggest that the HEPES buffer at pH 6.5 might yield more reproducible fluorescence emission measurements when DPA concentrations are between 100 ppt and 1 ppb.

In some embodiments, the solution mixture used to measure fluorescence emission from the tracer complexes described in this disclosure can have a pH of between 5.0 and 8.0 (for example, between 5.0 and 7.5, between 5.0 and 7.0, between 5.5 and 8.0, between 5.5 and 7.5, between 5.5 and 7.0, between 6.0 and 8.0, between 6.0 and 7.5, between 6.5 and 8.0, between 6.5 and 7.5, or any other range between 5.0 and 8.0).

As discussed above, in certain embodiments, the solution mixture used to measure fluorescence emission from the tracer complexes can include acetate ions. For example, the solution mixture can include acetate ions as part of a buffered composition. Acetate ions can be present as a sodium acetate buffered solution, an ammonium acetate buffered solution, or as part of a buffer composition in combination with one or more other cations such as, but not limited to, calcium, potassium, lithium, and magnesium.

(ii) Lanthanide Ion Concentration

Figure 10A:
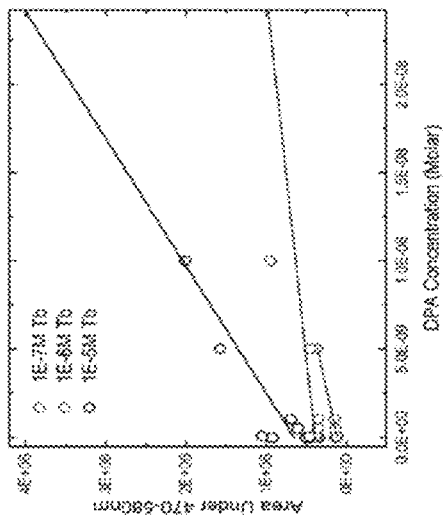
FIG. 10A is a graph showing fluorescence emission measurements as a function of DPA concentration for multiple solutions with different Tb ion concentrations.
Figure 10B:
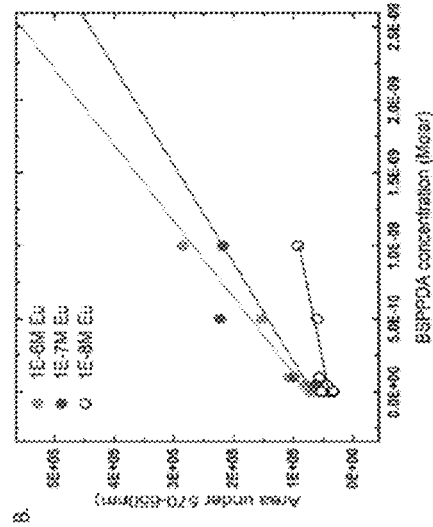
FIG. 10B is a graph showing an enlarged view of a portion of the graph in FIG. 10A.

Further investigations were performed to determine—with ammonium acetate used as the solvent for conducting fluorescence emission measurements—appropriate lanthanide ion concentrations to maintain a desired signal-to-noise ratio in the fluorescence emission measurements. Fluorescence measurements were performed in ammonium acetate solutions at various DPA:Tb concentration ratios (with 1:100 as the lowest ratio), with the Tb ion concentration held constant in each solution. FIG. 10A is a graph showing fluorescence emission measurements as a function of DPA concentration in each of the solutions. FIG. 10B shows an enlarged view of the region of FIG. 10A indicated by the dashed box. Based on these results, a Tb ion concentration of approximately $1 \times 10^{-5}$M appeared to yield measurements with the highest signal-to-noise ratio.

In some embodiments, to achieve suitable signal-to-noise ratios for measurement of fluorescence emission from tracer complexes, the Tb ion concentration is maintained between $1 \times 10^{-4}$M and $1 \times 10^{-6}$ M (for example, between $9.5 \times 10^{-5}$M and $1.5 \times 10^{-6}$ M, between $9.0 \times 10^{-5}$ M and $2.0 \times 10^{-6}$ M, between $8.5 \times 10^{-5}$M and $2.5 \times 10^{-6}$ M, between $8.0 \times 10^{-5}$ M and $3.0 \times 10^{-6}$ M, between $7.5 \times 10^{-5}$M and $3.5 \times 10^{-6}$ M, between $7.0 \times 10^{-5}$M and $4.0 \times 10^{-6}$ M, between $6.5 \times 10^{-5}$M and $4.5 \times 10^{-6}$ M, between $6.0 \times 10^{-5}$M and $5.0 \times 10^{-6}$ M, between $5.5 \times 10^{-5}$M and $5.5 \times 10^{-6}$ M, between $5.0 \times 10^{-5}$ M and $6.0 \times 10^{-6}$ M, between $4.5 \times 10^{-5}$M and $6.5 \times 10^{-6}$ M, between $4.0 \times 10^{-5}$M and $7.0 \times 10^{-6}$ M, between $3.5 \times 10^{-5}$ M and $7.5 \times 10^{-6}$ M, between $3.0 \times 10^{-5}$M and $8.0 \times 10^{-6}$ M, between $2.5 \times 10^{-5}$M and $8.5 \times 10^{-6}$ M, between $2.0 \times 10^{-5}$M and $9.0 \times 10^{-6}$ M, or any other range between $1 \times 10^{-4}$M and $1 \times 10^{-6}$ M).

Figure 11A:
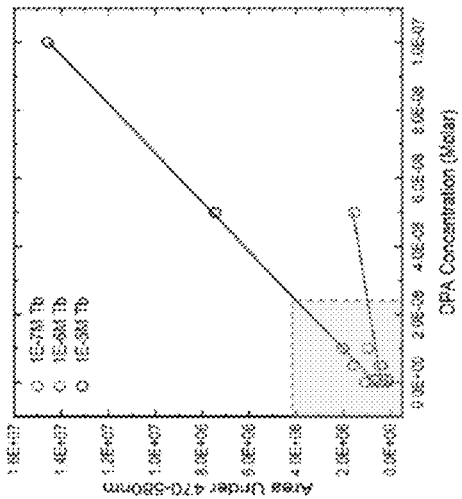
FIG. 11A is a graph showing fluorescence emission measurements as a function of BSPPDA concentration for multiple solutions with different Eu ion concentrations.
Figure 11B:
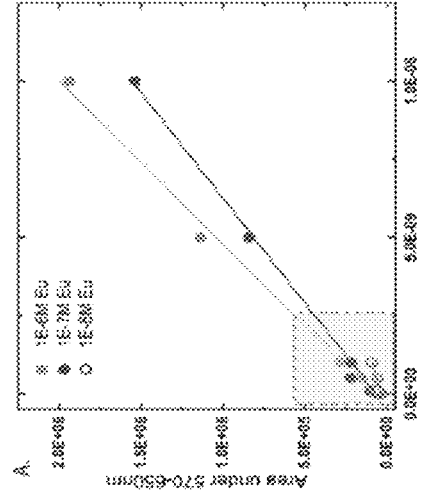
FIG. 11B is a graph showing an enlarged view of a portion of the graph in FIG. 11A.

Fluorescence measurements were also performed in ammonium acetate solutions at various BSPPDA:Eu concentration ratios (with 1:10 as the lowest ratio), with the Eu ion concentration held constant in each solution. FIG. 11A is a graph showing fluorescence emission measurements as a function of BSPPDA concentration in each of the solutions. FIG. 11B shows an enlarged view of the region of FIG. 11A indicated by the dashed box. Based on these results, a Eu ion concentration of approximately $1 \times 10^{-6}$ M appeared to yield measurements with the highest signal-to-noise ratio.

In certain embodiments, to achieve suitable signal-to-noise ratios for measurement of fluorescence emission from tracer complexes, the Tb ion concentration is maintained between $1 \times 10^{-5}$M and $1 \times 10^{-7}$M (for example, between $9.5 \times 10^{-6}$ M and $1.5 \times 10^{-7}$M, between $9.0 \times 10^{-6}$ M and $2.0 \times 10^{-7}$ M, between $8.5 \times 10^{-6}$ M and $2.5 \times 10^{-7}$M, between $8.0 \times 10^{-6}$ M and $3.0 \times 10^{-7}$ M, between $7.5 \times 10^{-7}$ M and $3.5 \times 10^{-7}$M, between $7.0 \times 10^{-6}$ M and $4.0 \times 10^{-7}$M, between $6.5 \times 10^{-6}$ M and $4.5 \times 10^{-7}$M, between $6.0 \times 10^{-6}$ M and $5.0 \times 10^{-7}$M, between $5.5 \times 10^{-6}$ M and $5.5 \times 10^{-7}$M, between $5.0 \times 10^{-6}$ M and $6.0 \times 10^{-7}$M, between $4.5 \times 10^{-6}$ M and $6.5 \times 10^{-7}$M, between $4.0 \times 10^{-6}$ M and $7.0 \times 10^{-7}$M, between $3.5 \times 10^{-6}$ M and $7.5 \times 10^{-7}$M, between $3.0 \times 10^{-6}$ M and $8.0 \times 10^{-7}$M, between $2.5 \times 10^{-6}$ M and $8.5 \times 10^{-7}$M, between $2.0 \times 10^{-6}$ M and $9.0 \times 10^{-7}$M, or any other range between $1 \times 10^{-5}$M and $1 \times 10^{-7}$M).

In some embodiments, to achieve suitable signal-to-noise ratios for measurement of fluorescence emission from tracer complexes, the lanthanide ion concentration is maintained between any of the foregoing combinations of range limiting values discussed above. For example, the lanthanide ion concentration can be maintained between $1 \times 10^{-4}$ M and $1 \times 10^{-7}$M (such as between $0.5 \times 10^{-4}$ M and $2.0 \times 10^{-7}$M, between $0.5 \times 10^{-4}$ M and $3.0 \times 10^{-7}$M, between $0.5 \times 10^{-4}$ M and $4.0 \times 10^{-7}$M, between $0.5 \times 10^{-4}$ M and $5.0 \times 10^{-7}$M, between $0.5 \times 10^{-4}$ M and $6.0 \times 10^{-7}$M, between $0.5 \times 10^{-4}$ M and $7.0 \times 10^{-7}$M, between $0.5 \times 10^{-4}$ M and $8.0 \times 10^{-7}$M, between $0.5 \times 10^{-4}$ M and $9.0 \times 10^{-7}$M, between $0.5 \times 10^{-4}$ M and $1.0 \times 10^{-6}$ M, between $0.5 \times 10^{-4}$ M and $2.0 \times 10^{-6}$ M, between $0.5 \times 10^{-4}$M and $3.0 \times 10^{-6}$ M, between $0.5 \times 10^{-4}$M and $4.0 \times 10^{-6}$ M, between $0.5 \times 10^{-4}$ M and $5.0 \times 10^{-6}$ M, between $0.5 \times 10^{-4}$ M and $6.0 \times 10^{-6}$ M, between $0.5 \times 10^{-4}$ M and $7.0 \times 10^{-6}$ M, between $0.5 \times 10^{-4}$ M and $8.0 \times 10^{-6}$ M, between $0.3 \times 10^{-4}$ M and $2.0 \times 10^{-7}$M, between $0.3 \times 10^{-4}$ M and $3.0 \times 10^{-7}$M, between $0.3 \times 10^{-4}$ M and $4.0 \times 10^{-7}$M, between $0.3 \times 10^{-4}$M and $5.0 \times 10^{-7}$M, between $0.3 \times 10^{-4}$M and $6.0 \times 10^{-7}$M, between $0.3 \times 10^{-4}$ M and $7.0 \times 10^{-7}$M, between $0.3 \times 10^{-4}$ M and $8.0 \times 10^{-7}$M, between $0.3 \times 10^{-4}$ M and $9.0 \times 10^{-7}$ M, between $0.3 \times 10^{-4}$ M and $1.0 \times 10^{-6}$ M, between $0.3 \times 10^{-4}$ M and $2.0 \times 10^{-6}$ M, between $0.3 \times 10^{-4}$ M and $3.0 \times 10^{-6}$ M, between $0.3 \times 10^{-4}$ M and $4.0 \times 10^{-6}$ M, between $0.3 \times 10^{-4}$ M and $5.0 \times 10^{-6}$ M, between $0.3 \times 10^{-4}$M and $6.0 \times 10^{-6}$ M, between $0.3 \times 10^{-4}$M and $7.0 \times 10^{-6}$ M, between $0.3 \times 10^{-4}$ M and $8.0 \times 10^{-6}$ M, between $0.7 \times 10^{-4}$ M and $2.0 \times 10^{-7}$M, between $0.7 \times 10^{-4}$ M and $3.0 \times 10^{-7}$M, between $0.7 \times 10^{-4}$ M and $4.0 \times 10^{-7}$M, between $0.7 \times 10^{-4}$ M and $5.0 \times 10^{-7}$ M, between $0.7 \times 10^{-4}$ M and $6.0 \times 10^{-7}$M, between $0.7 \times 10^{-4}$ M and $7.0 \times 10^{-7}$M, between $0.7 \times 10^{-4}$ M and $8.0 \times 10^{-7}$ M, between $0.7 \times 10^{-4}$M and $9.0 \times 10^{-7}$M, between $0.7 \times 10^{-4}$M and $1.0 \times 10^{-6}$ M, between $0.7 \times 10^{-4}$ M and $2.0 \times 10^{-6}$ M, between $0.7 \times 10^{-4}$ M and $3.0 \times 10^{-6}$ M, between $0.7 \times 10^{-4}$ M and $4.0 \times 10^{-6}$ M, between $0.7 \times 10^{-4}$ M and 5.0×10$^{-6}$ M, between 0.7×10$^{-4}$ M and 6.0×10$^{-6}$ M, between 0.7×10$^{-4}$ M and 7.0×10$^{-6}$ M, between 0.7×10$^{-4}$ M and 8.0×10$^{-6}$ M, and any other range between 1×10$^{-4}$ M and 1×10$^{-7}$M).

(iii) Lanthanide Ions and Tracer Species

In the preceding description, multiple different types of lanthanide elements can be added in step 106 to the separated components from step 104. In some embodiments, however, steps 106 and 108 can be combined, and a separation step can be performed after each type of lanthanide element is added to the separated components. For example, a first type of lanthanide element can be combined with the separated components as described above, and then each of the component solutions can be purified to remove excess quantities of the first type of lanthanide element using the second chromatographic separation device as described above. Next, a second type of lanthanide element can be added to each of the purified, separated components as described above, and then each of the component solutions can then be purified again to remove excess quantities of the second type of lanthanide element using the second chromatographic separation device. A similar procedure can be repeated for third, fourth, fifth, and additional different types of lanthanide elements that are added to the separated components.

This type of work flow in which different types of lanthanide elements are added sequentially can have certain advantages. Certain tracer species will bind to, but not sensitize, certain types of lanthanide ions. For example, BSPPDA generally will bind but not sensitize terbium ions. Different tracer species can then be distinguished based on their selective sensitization of different types of lanthanide ions.

Systems for Tracer Analysis

Figure 13:
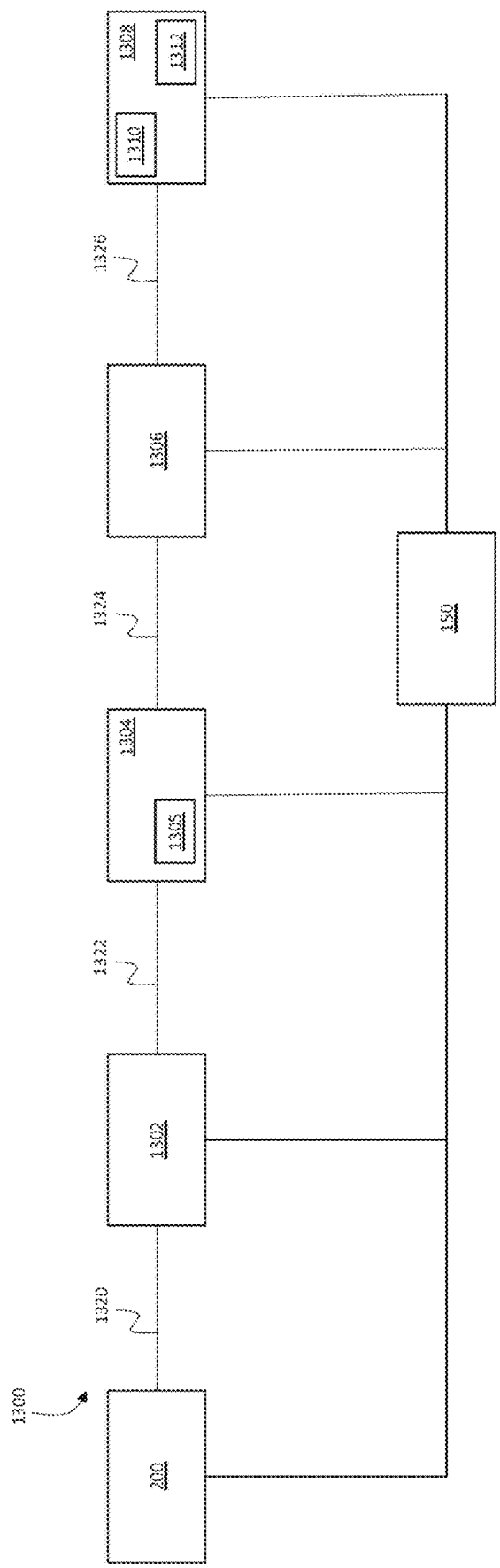
FIG. 13 is a schematic diagram of a system for analyzing groundwater samples from petroleum containing reservoirs.

FIG. 13 shows a schematic diagram of a system 1300 for analyzing organic tracer species in a groundwater sample from a petroleum containing reservoir. System 1300 includes a purification unit 200, a first chromatographic separation device 1302, a fluid source 1304, a second chromatographic separation device 1306, and an analyzer 1308. Each of these components is coupled to controller 150.

During operation of the system, purification unit 200 removes matrix and other substances from the groundwater sample. As described above, in some embodiments, purification unit 200 includes a solid phase extraction material onto which matrix substances are adsorbed. An aqueous fraction of the groundwater sample is first adsorbed onto, and then eluted from, the solid phase extraction material. The aqueous fraction is then conveyed from an outlet of purification unit 200 to an inlet of first chromatographic separation device 1302 via conduit 1320.

Figure 14:
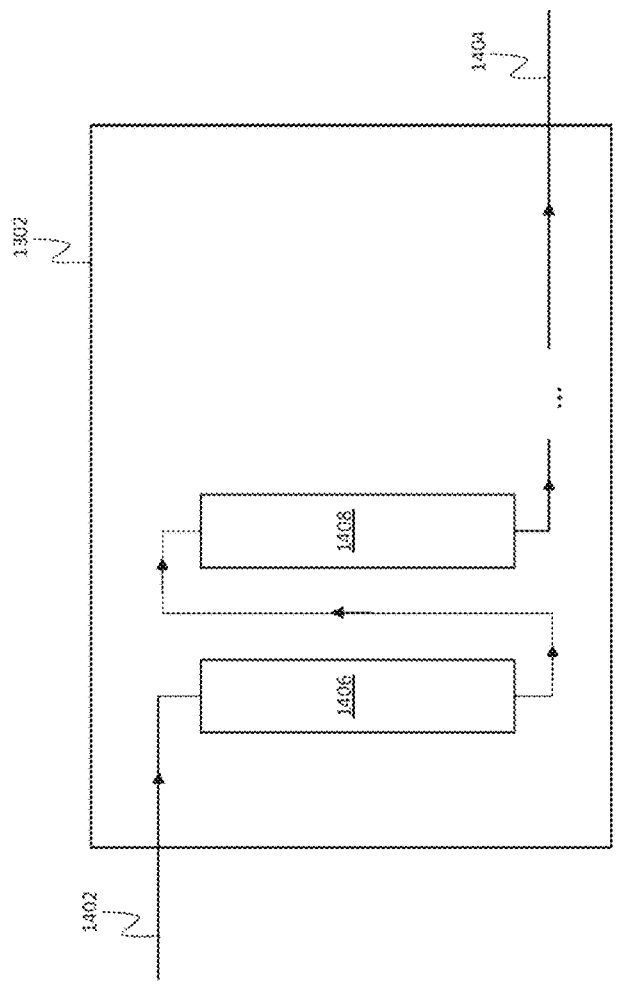
FIG. 14 is a schematic diagram of a chromatographic separation device.

First chromatographic separation device 1302 can include one or more chromatographic columns, as described above. If multiple columns are present, they can be connected in series so that some or all of the components eluted from an earlier column in the series can be selectively loaded onto and eluted from one or more later columns in the series. FIG. 14 shows a schematic diagram of an example of first chromatic separation device 1302. Device 1302 includes an inlet 1402, an outlet 1404, a first chromatography column 1406, and a second chromatography column 1408. Device 1302 can also include additional chromatography columns as described above. Fluid flow between columns 1406 and 1408 is indicated by the arrows in FIG. 14. After emerging from outlet 1404, separated components of the aqueous fraction are transported to fluid source 1304 through conduit 1322.

Figure 15:
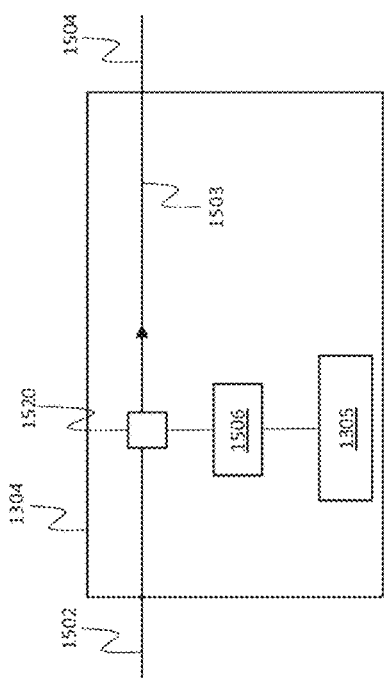
FIG. 15 is a schematic diagram of a fluid source.

Fluid source 1304 includes one or more fluid reservoirs 1305, and during operation of system 1300, delivers fluids that include lanthanide elements to the separated components generated by first chromatographic separation device 1302. FIG. 15 shows a schematic diagram of an example of a fluid source 1304. In addition to fluid reservoir 1305, fluid source 1304 includes an inlet 1502, an outlet 1504, and a flow regulator 1506. Fluid flow through conduit 1503 between inlet 1502 and outlet 1504 is indicated by the arrow in FIG. 15. Flow regulator 1506 can be connected to controller 150 (not shown).

During operation of fluid source 1304, controller 150 adjusts flow regulator 1506 so that a discrete volume of fluid that includes one or more lanthanide elements is delivered from fluid reservoir 1305 into conduit 1503. The lanthanide element(s) form complexes with tracer species in the component solutions flowing through conduit 1503 as described above, yielding component solutions with tracer:lanthanide complexes. These solutions emerge from outlet 1504 and are transported to second chromatographic separation device 1306 through conduit 1324.

In some embodiments, system 1300 includes a fluid mixer 1520. Fluid mixer 1520 can be implemented as part of fluid source 1304, as shown in FIG. 15. Alternatively, in some embodiments, fluid mixer 1520 is implemented as a separate component of system 1300, and is connected to fluid source 1304 and to the first chromatographic separation device 1302. Fluid mixer 1520 mixes the effluent stream from first chromatographic separation device 1302 with the lanthanide-containing fluid from fluid reservoir 1305 to form a solution mixture for analysis.

The manner in which the fluids are mixed in fluid mixer 1520 to achieve chelation of tracer ligands to lanthanide species can be an important aspect of system 1300. In particular, higher intensity fluorescence signals are generally measured as the extent of chelation of the lanthanide species by the tracer ligands increases. However, if mixing significantly increases temporal dispersion of analytes, then subsequent chromatographic sensitivity (peak height) and/or resolution can be compromised. If chromatographic separations of tracer complexes occur at lower resolution, fluorescence signal intensities can be reduced.

A variety of different fluid mixers can be used in system 1300. In some embodiments, in-line chelation can be accomplished using a post-chromatographic column reactor, which dampens pulsations from a fluid pump driving fluid flow. In addition, the reactor includes a mixing chamber that allows for sufficient residence time to complete chelation.

Figure 19E:
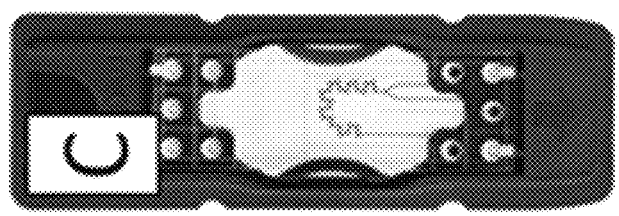
FIG. 19E is a schematic diagram of an example of a microfluidic fluid mixing chip.
Figure 19B:
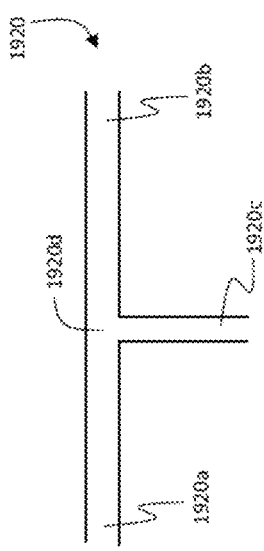
FIGS. 19B-19D are schematic diagrams of examples of fluid mixing junctions.
Figure 19C:
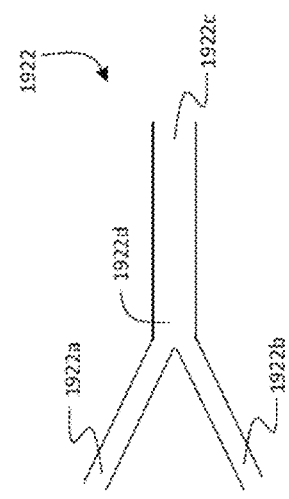
Figure 19D:
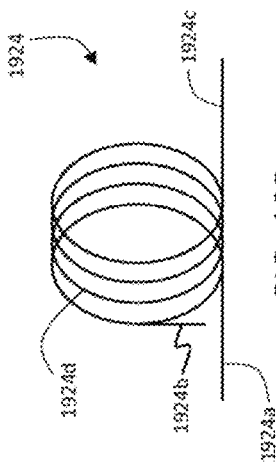
Figure 19A:
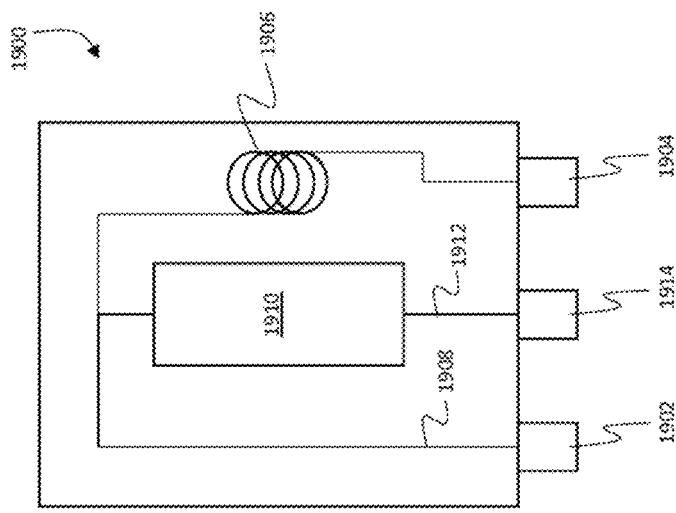
FIG. 19A is a schematic diagram of an example of a post-chromatography column reactor.

FIG. 19A shows a schematic diagram of an example of a post-chromatographic column reactor 1900. Reactor 1900 includes a first inlet 1902 that is connected to first chromatographic separation device 1302, and receives the effluent stream that includes tracer species. First inlet 1902 is connected to mixing chamber 1910 via conduit 1908. Reactor 1900 also includes a second inlet 1904 that receives the lanthanide-containing solution from fluid reservoir 1305. Second inlet 1904 is connected to mixing chamber 1910 via a pulsation dampener 1906. In reactor 1900, pulsation dampener 1906 is implemented as a coiled length of flexible tubing (formed from a material such as rubber or silicone), although more generally, a variety of different pulsation dampeners can be used.

During operation, the tracer-containing effluent solution and the lanthanide-containing solutions are mixed in mixing chamber 1910. After mixing, the combined solution is delivered to outlet 1914 via conduit 1912, from which the combined solution is transported to second chromatographic separation device 1306.

Certain commercially available reactors can be used in system 1300 to mix tracer-containing and lanthanide-containing solutions. An example of such a reactor is the Metrohm post column reactor 6.2836.000 (available from Metrohm AG, Germany).

In certain embodiments, a fluidic junction can be used as a fluid mixer. Examples of such junctions include, but are not limited to, T-shaped junctions, Y-shaped junctions, and fluid-loop junctions. FIG. 19B shows an example of a T-shaped mixing junction 1920. Junction 1920 includes a first inlet 1920a that is connected to first chromatographic separation device 1302, a second inlet 1920b that is connected to fluid reservoir 1305, and an outlet 1920c that is connected to second chromatographic separation device 1306. Fluid mixing occurs at, and downstream from, junction region 1920d.

FIG. 19C shows an example of a Y-shaped mixing junction 1922. Junction 1922 includes a first inlet 1922a that is connected to first chromatographic separation device 1302, a second inlet 1922b that is connected to fluid reservoir 1305, and an outlet 1922c that is connected to second chromatographic separation device 1306. Fluid mixing occurs at, and downstream from, junction region 1922d.

FIG. 19D shows an example of a fluid-loop mixing junction 1924. Junction 1924 includes a first inlet 1924a that is connected to first chromatographic separation device 1302, a second inlet 1924b that is connected to fluid reservoir 1305, and an outlet 1924c that is connected to second chromatographic separation device 1306. As shown in FIG. 19D, second inlet 1924b is connected to a looped conduit 1924d, allowing the lanthanide-containing solution to be introduced into looped conduit 1924d as it propagates along a direction that is approximately opposite to the direction of propagation of the effluent from first chromatographic separation device 1302.

In some embodiments, the fluid mixer can be implemented as a mixing chip. A variety of mixing chips with different configurations can be used. As one example, in certain embodiments, fluid mixer 1520 can be implemented as a microfluidic chip with a teardrop-shaped mixing channel. FIG. 19E shows a schematic diagram of such a chip.

To evaluate the feasibility of using different fluid mixers, three different fluid mixing devices were investigated: a mixing T-junction, similar to junction 1920 in FIG. 19B; a post-chromatography column reactor, the Metrohm 6.2836.000 described above; and the microfluidic mixing chip shown in FIG. 19E.

For the mixing T-junction, a pulsation dampener was constructed by connecting a short piece of 0.5 mm capillary, capped at one end, to the outlet of a pump driving transport of the lanthanide-containing solution, using a tee. The other side of the tee was connected to the T-junction fluid mixer with a 0.12 mm capillary to increase the backpressure on the pump and reduce ripple. The outlet of the T-junction fluid mixer was connected to a detector flow cell, and then to waste.

For the post-chromatography column reactor, to reduce peak dispersion, the reactor was installed in such a way to minimize the length of capillary between the column and reactor, and between the reactor and the detector. A wide capillary (0.5 mm diameter) was used at the reactor outlet to reduce the backpressure on the reactor.

Based on static experiments, suitable conditions for fluorescence measurement of DPA concentration were 1 M acetate buffer, with $10^{-6}$ $Tb^{3+}$ and up to 30% acetonitrile. Therefore, the final solution after mixing was targeted to have these characteristics. The final solution is prepared by mixing a lanthanide-containing solution and the effluent solution (the chromatographic mobile phase) from the first chromatographic separation device, according to a mixing ratio between two solutions. In principle, the optimum mixing ratio maximizes chelation of the lanthanide species by the tracer ligands, while ensuring that dilution of the chromatographic mobile phase is minimized. Three different mixing ratio conditions, shown in Table 1, were investigated, while ensuring that the final lanthanide and sodium acetate concentrations remained constant.

| Volume Mixing Ratio | Buffer Solution | Final Concentrations |
|---|---|---|
| 1:1 | 2M NaOAc, $2 \times 10^{-6}$M $TbCl_3$ | 1M NaOAc, $1 \times 10^{-6}$M $TbCl_3$ |
| 2:1 | 1.5M NaOAc, $1.5 \times 10^{-6}$M $TbCl_3$ | 1M NaOAc, $1 \times 10^{-6}$M $TbCl_3$ |
| 1:4 | 5M NaOAc, $5 \times 10^{-6}$M $TbCl_3$ | 1M NaOAc, $1 \times 10^{-6}$M $TbCl_3$ |

It was observed that mixing ratios did not measurably affect the peak intensity of the measured fluorescence emission. However, at a mixing ratio of 2:1, the baseline fluctuation was reduced in comparison to the 1:1 and 1:4 mixing ratios. This mixing ratio was selected for measurement of fluorescence emission intensity in certain experiments, as described below.

As discussed previously, it was determined that up to 0.5% TFA and up to 30% acetonitrile can be added to the buffer solution without significantly impacting the fluorescence sensitivity. Therefore, to assess the limit of detection (LOD) of the system, the aqueous phase (A) selected for chromatographic separation was water with TFA, and the organic phase (B) was acetonitrile. Additionally, it was determined that a TFA concentration of only 0.1% would be adequate for the chromatographic separation operation, giving a pH of less than 2.2 which is sufficient to protonate both carboxylic acid groups of DPA.

An Agilent Poroshell EC-C18 column, 2.1×150 mm, maintained at a temperature of 40° C., was used to chromatographically separate tracer complexes for purposes of assessing LOD. The high performance liquid chromatography (HPLC) separation was run in gradient mode, starting from 10% B, and increasing to 30% B over a time of 10 minutes. The column was then flushed with 100% B for 5 minutes. Due to the immiscibility of high acetonitrile concentrations with the acetate buffer, the buffer pump was programmed to stop during the flushing part of the run, and resume during the post-run equilibration for 2 minutes.

Figure 20:
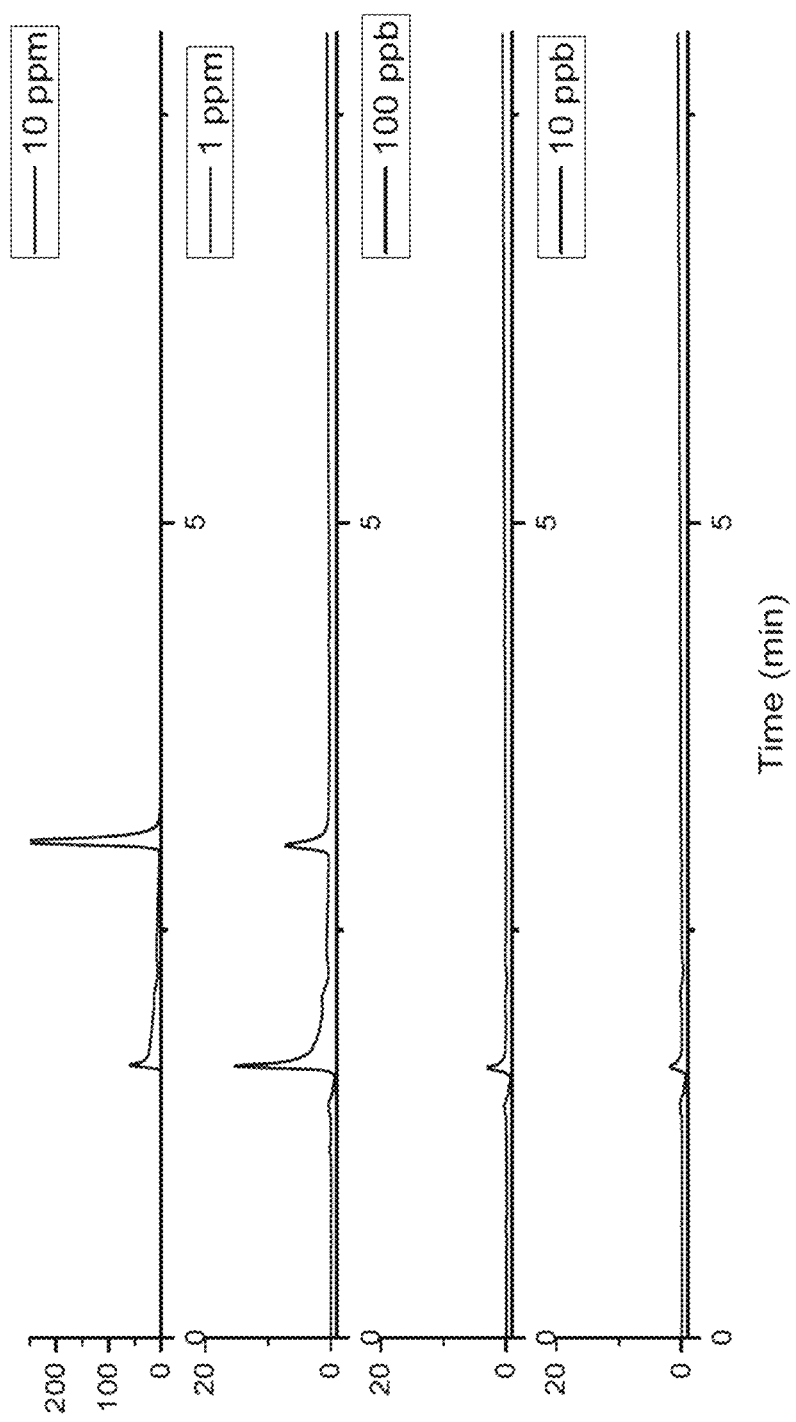
FIG. 20 is a graph showing measured fluorescence chromatograms for a set of DPA samples of different concentration, mixed using a microfluidic mixing chip.

To assess the LOD when using the microfluidic mixing chip shown in FIG. 19E, a series of DPA samples were injected at concentrations ranging from 10 ppm to 10 ppb. Measured fluorescence emission intensity chromatograms of the DPA samples are shown in FIG. 20. DPA concentrations as small as 1 ppm were easily detected in the chromatograms (at an elution time of approximately 3.1 minutes), but DPA concentrations of 100 ppb and smaller were not detected. This LOD is comparable to the detection limit of a diodearray UV absorbance detector, suggesting that the advantages of tracer-based detection are not fully realized under these conditions.

To improve the sensitivity of the system, the mixing chip was replaced by the Metrohm post column reactor 6.2836.000 discussed above. This increased post-mixing residence time from about 0.03 min to about 0.5 min. Also, a degassing membrane filter (obtained from Whatman, Maidstone, UK) was added to remove dissolved gas bubbles from the buffer solution. The acetate buffer solution was replaced with a 1 M sodium acetate solution (pH approximately 9), and the $Tb^{3+}$ concentration was adjusted to 5 µM. The flow rate of the acetate solution was lowered to 0.5 mL/min.

Figure 21:
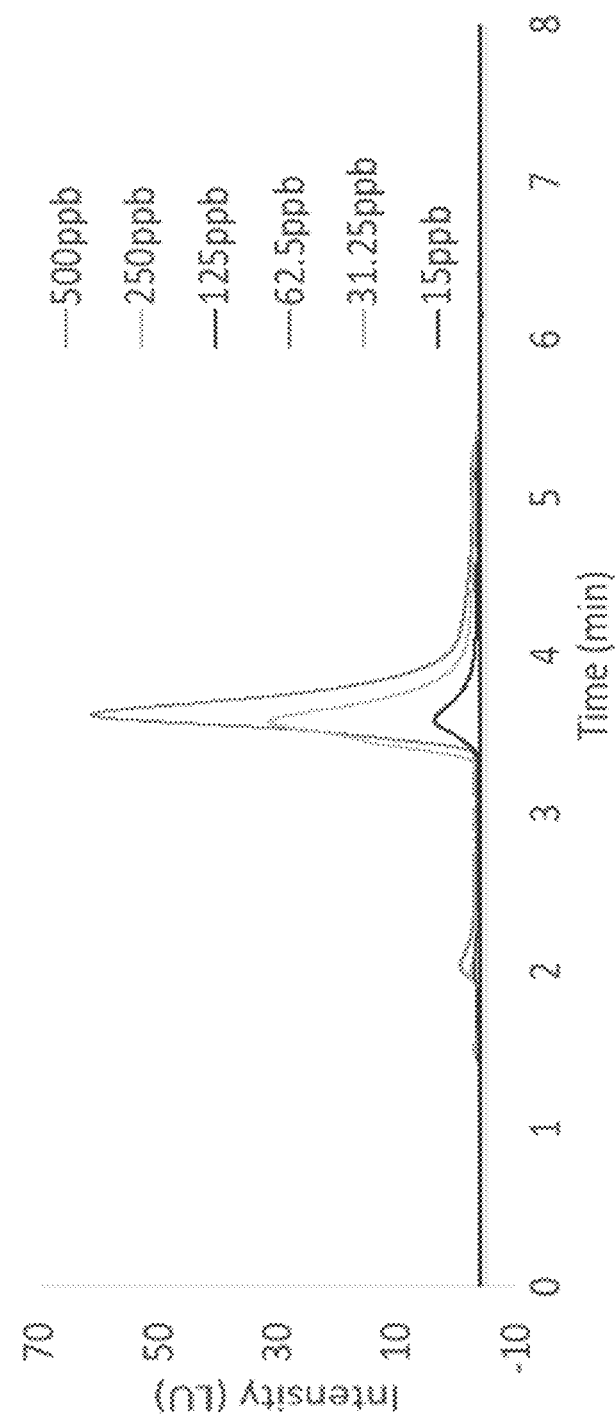
FIG. 21 is a graph showing measured chromatograms of a series of DPA samples at different DPA concentrations, mixed in a post-chromatographic column reactor.

FIG. 21 shows overlaid chromatograms of a series of DPA solutions, at DPA concentrations from 500 ppb to 15 ppb. The limit of detection was determined to be approximately 125 ppb. When coupled with solid phase extraction (SPE) at a typical pre-concentration factor of 200×, detection of sub-1 ppb concentrations of tracer species in the reservoir fluids is possible.

Returning to FIG. 13, second chromatographic separation device 1306 can generally include one or more chromatographic columns. In some embodiments, for example, second chromatographic separation device 1306 includes components that are similar to those of first chromatographic separation device 1302 as shown in FIG. 14. During operation, second chromatographic separation device 1306 separates excess quantities of one or more lanthanide elements from the separated components of the groundwater sample, and discharges purified separated components into conduit 1326, through which they are transported to analyzer 1308 for quantitative analysis.

As described above, in some embodiments, analyzer 1308 is configured to measure fluorescence emission from the separated components of the sample and can include a radiation source 1310 and a detector 1312, each of which is connected directly or indirectly to controller 150. During operation of analyzer 1308, controller 150 directs radiation source 1310 to expose each separated component to illumination radiation and directs detector 1312 to measure fluorescence emission from each separated component as described above. The raw fluorescence emission measurement information is transmitted to controller 150, which analyzes the information to determine relative amounts or concentrations of the tracer species in the groundwater sample.

Suitable radiation sources include, but are not limited to, incandescent sources, fluorescent sources, LED-based sources, laser diodes, lasers including, but not limited to, gas-based lasers, solid-state lasers, and dye-based lasers, metal-vapor and metal halide lamps, flash lamps, and other common radiation sources. Suitable detectors include, but are not limited to, photodiodes, charge-coupled devices (CCDs), CMOS-based detectors, photomultipliers, and arrays of any of the foregoing devices.

To assess the effectiveness of in-line fluid mixers independent of the chromatographic separation devices, samples of the mobile phase stream from the first chromatographic separation device 1302 (with no tracer species present) were injected with 50 mL aliquots of DPA solutions of differing DPA concentration. The mobile phase stream was a 90:10 mixture of (A) 0.1% TFA in water, and (B) acetonitrile. The mobile phase stream flowed into the post column reactor at a rate of 0.5 mL/min. A lanthanide-containing solution of a 1 M sodium acetate buffer (at a pH of approximately 9) and containing $TbCl_3$ at a concentration of 5 µM was introduced into the post column reactor at a flow rate of 0.5 mL/min. Following mixing of the solutions, fluorescence emission measurements were performed on each sample as described above.

Figure 22B:
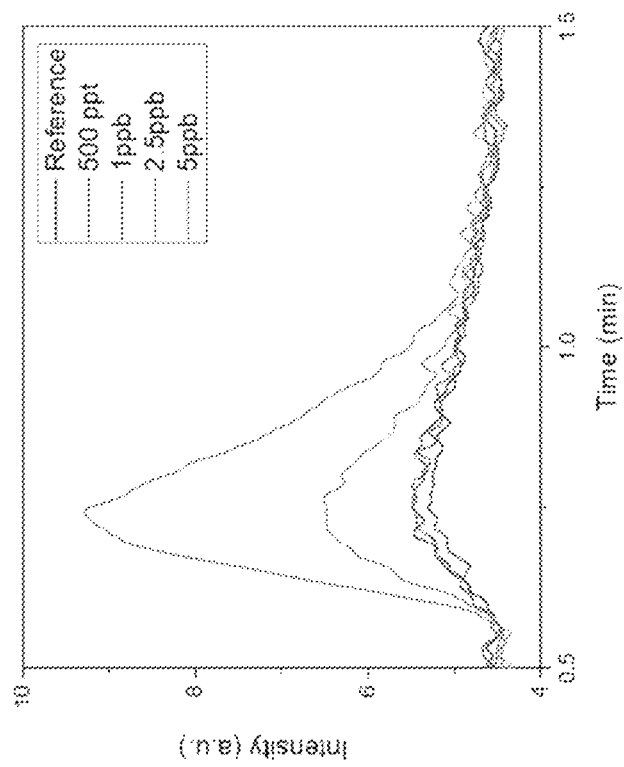
FIG. 22B is a graph showing an enlarged view of some of the chromatograms of FIG. 22A.
Figure 22A:
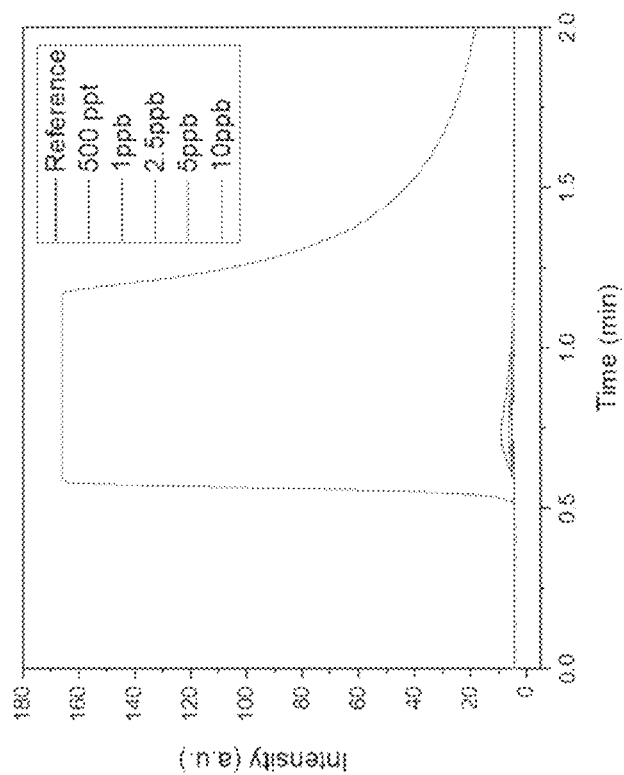
FIG. 22A is a graph showing measured chromatograms of a series of DPA samples injected directly into a fluid mixer, without performing a chromatographic separation.

FIG. 22A shows measured fluorescence chromatograms for the samples, and FIG. 22B shows all but one (10 ppb) of the chromatograms of FIG. 22A on an enlarged scale. Based on the data in FIGS. 22A and 22B, the LOD was about 2.5 ppb, which was comparable to the LOD determined during characterization of the detector used to measure fluorescence emission (an Agilent 1260 time-gated fluorescence detector).

Hardware and Software Implementation

Figure 12:
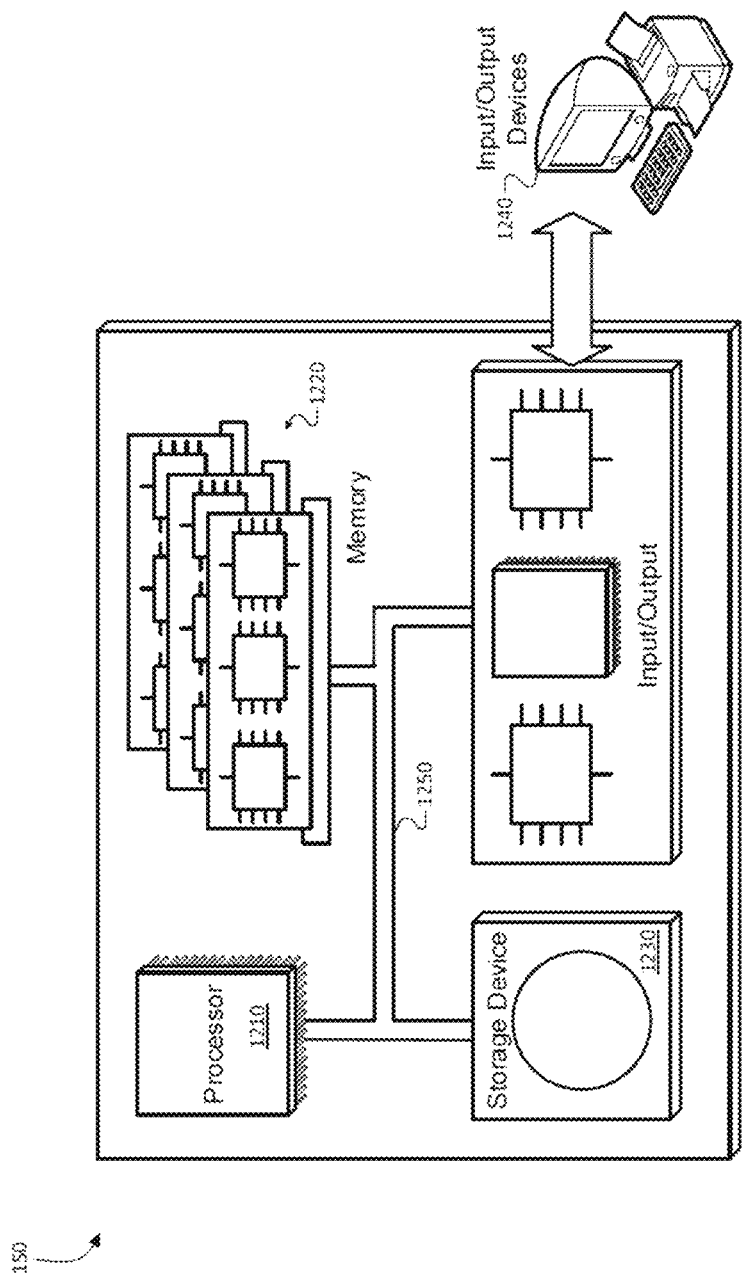
FIG. 12 is a schematic diagram of a controller.

Any of the sample processing steps and control functions described above can be executed by controller 150, or by another system controller, connected to any of the system components discussed herein, and to other components such as pumps, valves, optical components, and fluid handling components. In general, controller 150 can include a single electronic processor, multiple electronic processors, one or more integrated circuits (such as application specific integrated circuits), and any combination of the foregoing elements. Software instructions and hardware-based instructions are executed by controller 150 to perform the steps and functions discussed above. As shown in FIG. 12, controller 150 can include a processor 1210 and a data storage system (including memory 1220, storage elements such as a storage device 1230), interconnected using a system bus 1250. Controller 150 can be connected to at least one input device, and at least one output device, such as a display 1240. Each set of software-based instructions, embodied as a software program stored on a tangible, non-transient storage medium (for example, an optical storage medium such as a CD-ROM or DVD, a magnetic storage medium such as a hard disk, or a persistent solid state storage medium) or device, can be implemented in a high-level procedural or object-oriented programming language, or an assembly or machine language.

OTHER EMBODIMENTS

While this specification contains many specific implementation details, these should not be construed as limitations on the scope of the disclosure or on the scope of what may be claimed, but rather as descriptions of features that may be specific to particular embodiments. Features that are described in this specification in the context of separate embodiments can also be implemented in combination in a single embodiment unless expressly stated otherwise. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. Moreover, the separation of various system modules and components in the embodiments described above should not be understood as requiring such separation in all embodiments.

While particular embodiments have been described above, other embodiments are within the scope of the following claims.

What is claimed is:

1. A method, comprising:
   obtaining a groundwater sample comprising multiple organic tracer species from a petroleum containing reservoir;
   isolating an aqueous fraction of the groundwater sample;
   separating the aqueous fraction into a plurality of separated components, wherein each separated component comprises only one of the organic tracer species;
   individually combining each of the separated components with at least one lanthanide element to form a plurality of separated component solutions, wherein a ratio of the at least one lanthanide element to the only one of the organic tracer species in each of the separated component solutions is 10:1 or greater; and
   analyzing each separated component solution to determine a relative amount of each organic tracer species in the groundwater sample.

2. The method of claim 1, wherein the multiple organic tracer species comprise at least one of 2,6-pyridine dicarboxylic acid or a derivative of 2,6-pyridine dicarboxylic acid.

3. The method of claim 1, wherein the multiple organic tracer species comprise at least one of 4,7-bis(sulfonatophenyl)-1,10-phenanthroline-2,9-dicarboxylic acid or a derivative of 4,7-bis(sulfonatophenyl)-1,10-phenanthroline-2,9-dicarboxylic acid.

4. The method of claim 1, wherein isolating the aqueous fraction of the groundwater sample comprises extracting solid material from the groundwater sample.

5. The method of claim 1, wherein isolating the aqueous fraction of the ground water sample comprises removing one or more ionic species from the aqueous fraction, wherein the one or more ionic species comprise ions that are complexed by one or more of the multiple organic tracers species.

6. The method of claim 1, wherein isolating the aqueous fraction comprises increasing a concentration of at least one of the multiple organic tracer species in the aqueous fraction, relative to a concentration of the at least one species in the groundwater sample.

7. The method of claim 6, further comprising measuring retention times of the multiple organic tracers species on a chromatography column, and identifying at least one of the multiple organic tracer species based on its corresponding retention time.

8. The method of claim 1, wherein separating the aqueous fraction into a plurality of separated components comprises:
   performing a first chromatographic separation to separate the aqueous fraction into a first plurality of separated chromatographic fractions; and
   performing a second chromatographic separation of at least some members of the first plurality of separated chromatographic fractions to obtain the plurality of separated components.

9. The method of claim 8, wherein the first chromatographic separation is performed on a first chromatography column and the second chromatographic separation is performed on a second chromatography column having a chemical selectivity that differs from a chemical selectivity of the first chromatography column.

10. The method of claim 1, wherein the at least one lanthanide element comprises two or more lanthanide elements.

11. The method of claim 1, wherein the at least one lanthanide element comprises terbium, and wherein at least one of the separated component solutions comprises a complex formed of terbium and 2,6-pyridine dicarboxylic acid or a derivative thereof.

12. The method of claim 11, wherein the at least one of the separated component solutions comprising the complex formed of terbium and 2,6-pyridine dicarboxylic acid or a derivative thereof further comprises an ammonium acetate buffer.

13. The method of claim 11, wherein the ratio of terbium to 2,6-pyridine dicarboxylic acid or a derivative thereof in the at least one of the separated component solutions is 10:1 or greater.

14. The method of claim 1, wherein a first separated component solution comprises a complex formed of terbium and a first derivative of 2,6-pyridine dicarboxylic acid, and a second separated component solution comprises a complex formed of terbium and 2,6-pyridine dicarboxylic acid or a second derivative of 2,6-pyridine dicarboxylic acid different from the first derivative.

15. The method of claim 1, wherein at least one of the separated component solutions comprises a complex formed of europium and 4,7-bis(sulfonatophenyl)-1,10-phenanthroline-2,9-dicarboxylic acid or a derivative thereof.

16. The method of claim 15, wherein the ratio of europium to 4,7-bis(sulfonatophenyl)-1,10-phenanthroline-2,9-dicarboxylic acid or a derivative thereof in the at least one of the separated component solutions is 10:1 or greater.

17. The method of claim 15, wherein a first separated component solution comprises a complex formed of europium and a first derivative of 4,7-bis(sulfonatophenyl)-1,10-phenanthroline-2,9-dicarboxylic acid, and a second separated component solution comprises a complex formed of europium and 4,7-bis(sulfonatophenyl)-1,10-phenanthroline-2,9-dicarboxylic acid or a second derivative of 4,7-bis(sulfonatophenyl)-1,10-phenanthroline-2,9-dicarboxylic acid different from the first derivative.

18. The method of claim 1, further comprising, prior to analyzing each separated component solution, purifying each separated component solution to remove an excess quantity of the at least one lanthanide element from each separated component solution,
   wherein the purifying comprises, for each separated component solution, chromatographically separating the excess quantity of the at least one lanthanide element from the organic tracer species of the separated component solution; and
   wherein the method further comprises identifying the organic tracer species of each separated component solution based on a retention time of each separated component solution on a chromatography column used to perform the chromatographic separation.

19. The method of claim 1, wherein analyzing each separated component solution comprises measuring a quantity of fluorescence emission from a complex of the organic tracer species of the separated component solution and one of the at least one lanthanide elements, and determining an estimate of an amount of the organic tracer species in the groundwater sample based on the quantity of fluorescence emission.

20. The method of claim 19, wherein measuring the quantity of fluorescence emission comprises:
   exposing the separated component solution to illumination radiation, and terminating the exposure at an initial time $t_0$; and at a time $t_m > t_0$, detecting the fluorescence emission from the separated component solution,
wherein $(t_m - t_0)$ is 2 microseconds or more.

21. The method of claim 6, wherein separating the aqueous fraction into a plurality of separated components comprises:
  performing a first chromatographic separation to separate the aqueous fraction into a first plurality of separated chromatographic fractions; and
  performing a second chromatographic separation of at least some members of the first plurality of separated chromatographic fractions to obtain the plurality of separated components.

22. The method of claim 10, wherein separating the aqueous fraction into a plurality of separated components comprises:
  performing a first chromatographic separation to separate the aqueous fraction into a first plurality of separated chromatographic fractions; and
  performing a second chromatographic separation of at least some members of the first plurality of separated chromatographic fractions to obtain the plurality of separated components.

23. The method of claim 11, wherein separating the aqueous fraction into a plurality of separated components comprises:
  performing a first chromatographic separation to separate the aqueous fraction into a first plurality of separated chromatographic fractions; and
  performing a second chromatographic separation of at least some members of the first plurality of separated chromatographic fractions to obtain the plurality of separated components.

24. The method of claim 12, wherein separating the aqueous fraction into a plurality of separated components comprises:
  performing a first chromatographic separation to separate the aqueous fraction into a first plurality of separated chromatographic fractions; and
  performing a second chromatographic separation of at least some members of the first plurality of separated chromatographic fractions to obtain the plurality of separated components.

25. The method of claim 13, wherein separating the aqueous fraction into a plurality of separated components comprises:
  performing a first chromatographic separation to separate the aqueous fraction into a first plurality of separated chromatographic fractions; and
  performing a second chromatographic separation of at least some members of the first plurality of separated chromatographic fractions to obtain the plurality of separated components.

26. The method of claim 14, wherein separating the aqueous fraction into a plurality of separated components comprises:
  performing a first chromatographic separation to separate the aqueous fraction into a first plurality of separated chromatographic fractions; and
  performing a second chromatographic separation of at least some members of the first plurality of separated chromatographic fractions to obtain the plurality of separated components.

27. The method of claim 15, wherein separating the aqueous fraction into a plurality of separated components comprises:
  performing a first chromatographic separation to separate the aqueous fraction into a first plurality of separated chromatographic fractions; and
  performing a second chromatographic separation of at least some members of the first plurality of separated chromatographic fractions to obtain the plurality of separated components.

28. The method of claim 18, wherein separating the aqueous fraction into a plurality of separated components comprises:
  performing a first chromatographic separation to separate the aqueous fraction into a first plurality of separated chromatographic fractions; and
  performing a second chromatographic separation of at least some members of the first plurality of separated chromatographic fractions to obtain the plurality of separated components.

29. The method of claim 19, wherein separating the aqueous fraction into a plurality of separated components comprises:
  performing a first chromatographic separation to separate the aqueous fraction into a first plurality of separated chromatographic fractions; and
  performing a second chromatographic separation of at least some members of the first plurality of separated chromatographic fractions to obtain the plurality of separated components.

30. The method of claim 20, wherein separating the aqueous fraction into a plurality of separated components comprises:
  performing a first chromatographic separation to separate the aqueous fraction into a first plurality of separated chromatographic fractions; and
  performing a second chromatographic separation of at least some members of the first plurality of separated chromatographic fractions to obtain the plurality of separated components.

\* \* \* \* \*